United States Patent [19]

McGreevy et al.

[11] Patent Number: 4,781,175
[45] Date of Patent: Nov. 1, 1988

[54] ELECTROSURGICAL CONDUCTIVE GAS STREAM TECHNIQUE OF ACHIEVING IMPROVED ESCHAR FOR COAGULATION

[75] Inventors: Francis T. McGreevy, Aurora; Carol Bertrand; Karl W. Hahn, both of Englewood, all of Colo.

[73] Assignee: C. R. Bard, Inc., Murray Hills, N.J.

[21] Appl. No.: 849,950

[22] Filed: Apr. 8, 1986

[51] Int. Cl.$^4$ .............................................. A61B 17/39
[52] U.S. Cl. ............................ 128/303.17; 219/121.5; 219/121.51
[58] Field of Search ...................... 128/303.13, 303.14, 128/303.17, 303.1; 215/74, 75, 121 P, 121 PC, 121 PP, 121 PQ, 121 PR, 121 PU, 121 PV, 121 PW, 121 PT

[56] References Cited

U.S. PATENT DOCUMENTS

| 3,649,805 | 3/1972 | Rohrberg | 219/121 PP |
| 3,838,242 | 9/1974 | Goucher | 128/303.1 X |
| 3,903,891 | 9/1975 | Brayshaw | 128/303.14 |
| 3,991,764 | 11/1976 | Incropera et al. | 219/121 P X |
| 4,040,426 | 8/1977 | Morrison, Jr. | 128/303.17 |
| 4,060,088 | 11/1977 | Morrison, Jr. et al. | 219/121 PQ X |
| 4,188,927 | 2/1980 | Harris | 128/303.14 |
| 4,209,018 | 6/1980 | Meinke et al. | 128/303.17 |
| 4,271,837 | 6/1981 | Schuler | 128/303.14 |
| 4,378,801 | 4/1983 | Ooster | 128/303.14 |
| 4,429,694 | 2/1984 | McGreevy | 128/303.14 |
| 4,562,838 | 1/1986 | Walker | 128/303.14 |

FOREIGN PATENT DOCUMENTS

| 3119735 | 1/1983 | Fed. Rep. of Germany | 128/303.13 |
| 671497 | 5/1952 | United Kingdom . | |
| 1014995 | 12/1965 | United Kingdom . | |
| 1165148 | 9/1969 | United Kingdom | 128/303.17 |

OTHER PUBLICATIONS

Kimura et al., "Use of Gas Jet . . . Photocoagulation", IEEE Trans. Bio. Med. Eng., vol. BME-25, No. 3, May 1975, p. 218.
Lanzafame et al., "The Effect of $CO_2$ Laser . . . ", Lasers in Surgery & Med., 6:103-105, 1986.
Payne et al., "Evaluation of the Plasma Scalpel . . . ", Surg. Neurol., vol. 12, pp. 247-250, Sep. 1979.
Hishimoto, "Some Technical Problems . . . Hepatectomy", App. of Lasers, Jul. 1969.
Dennis et al., "Evaluation of Electrofulguration . . . ", Digestive Diseases and Sciences, vol. 24, No. 11, pp. 845-848, Nov. 1979.

*Primary Examiner*—Lee S. Cohen
*Attorney, Agent, or Firm*—John R. Ley

[57] ABSTRACT

An electrosurgical technique of achieving coagulation involves conducting a predetermined ionizable gas in a jet to the tissue at a predetermined flow rate sufficient to clear natural fluids from the tissue and to substantially expose the tissue stroma. Electrical radio frequency energy is conducted to the tissue in ionized conductive pathways in the gas jet. To achieve fulguration, the electrical energy is conducted as arcs in the ionized conductive pathways. To achieve a non-contact type of electrosurgical desiccation, the electrical energy is conducted as a non-arcing diffuse current in the ionized conductive pathways.

59 Claims, 23 Drawing Sheets

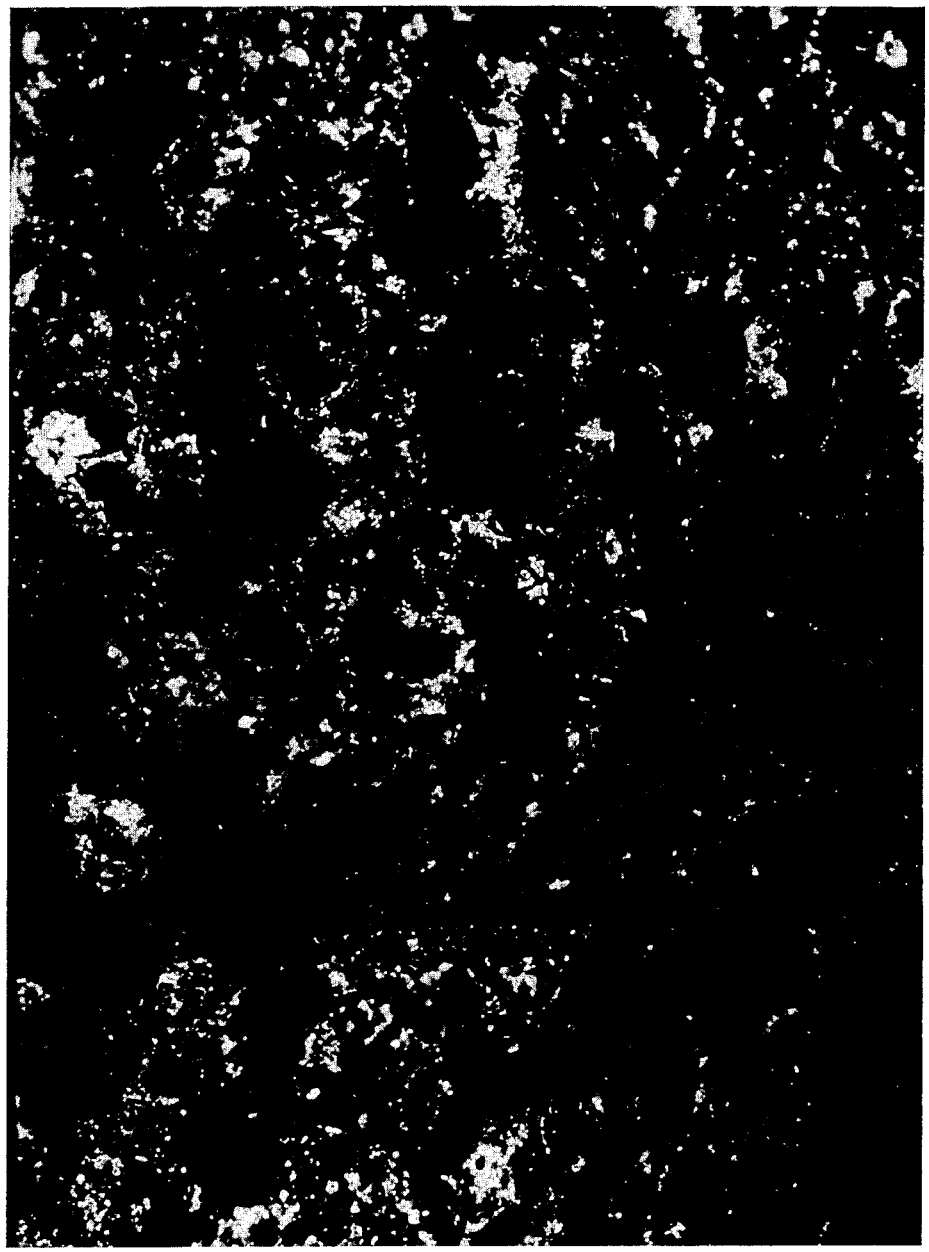
Fig_1

Fig_2

Fig_3A

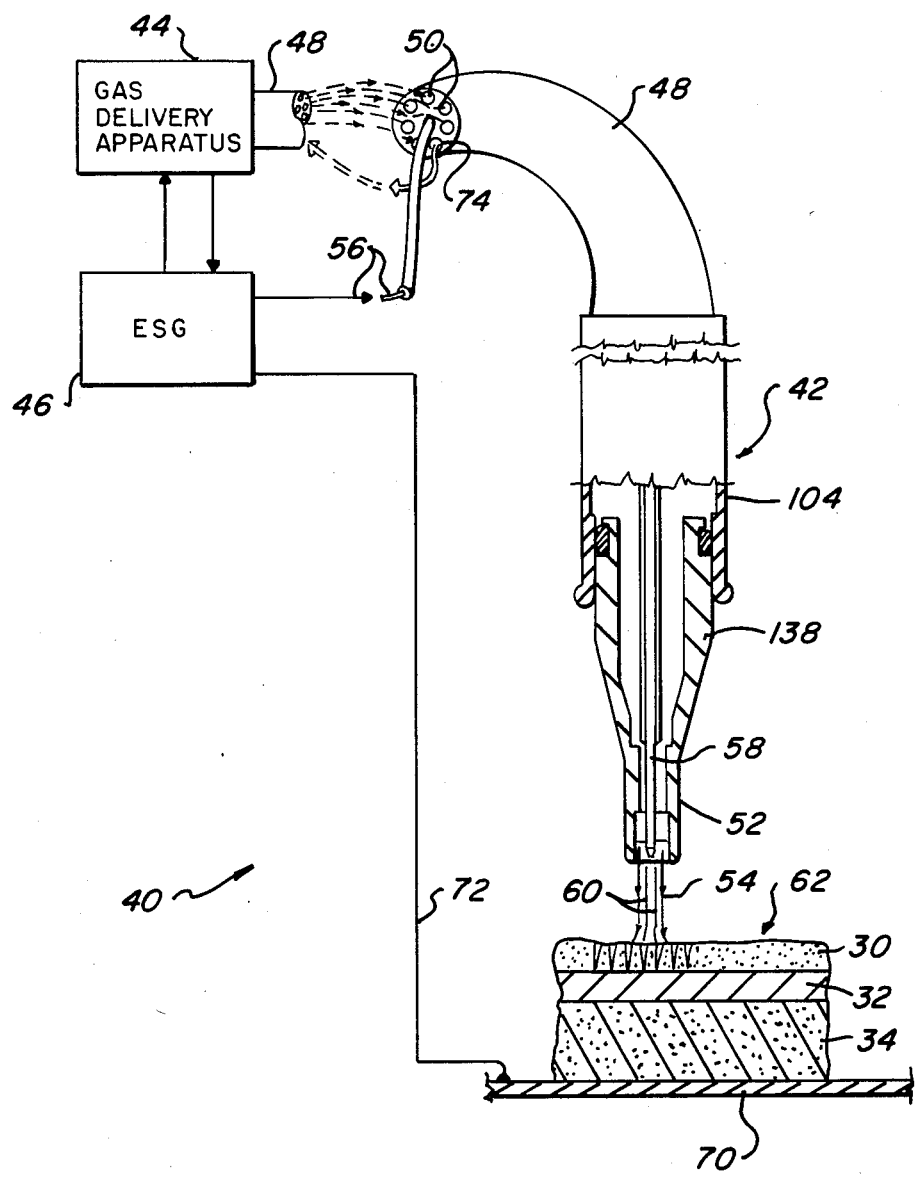
Fig_4

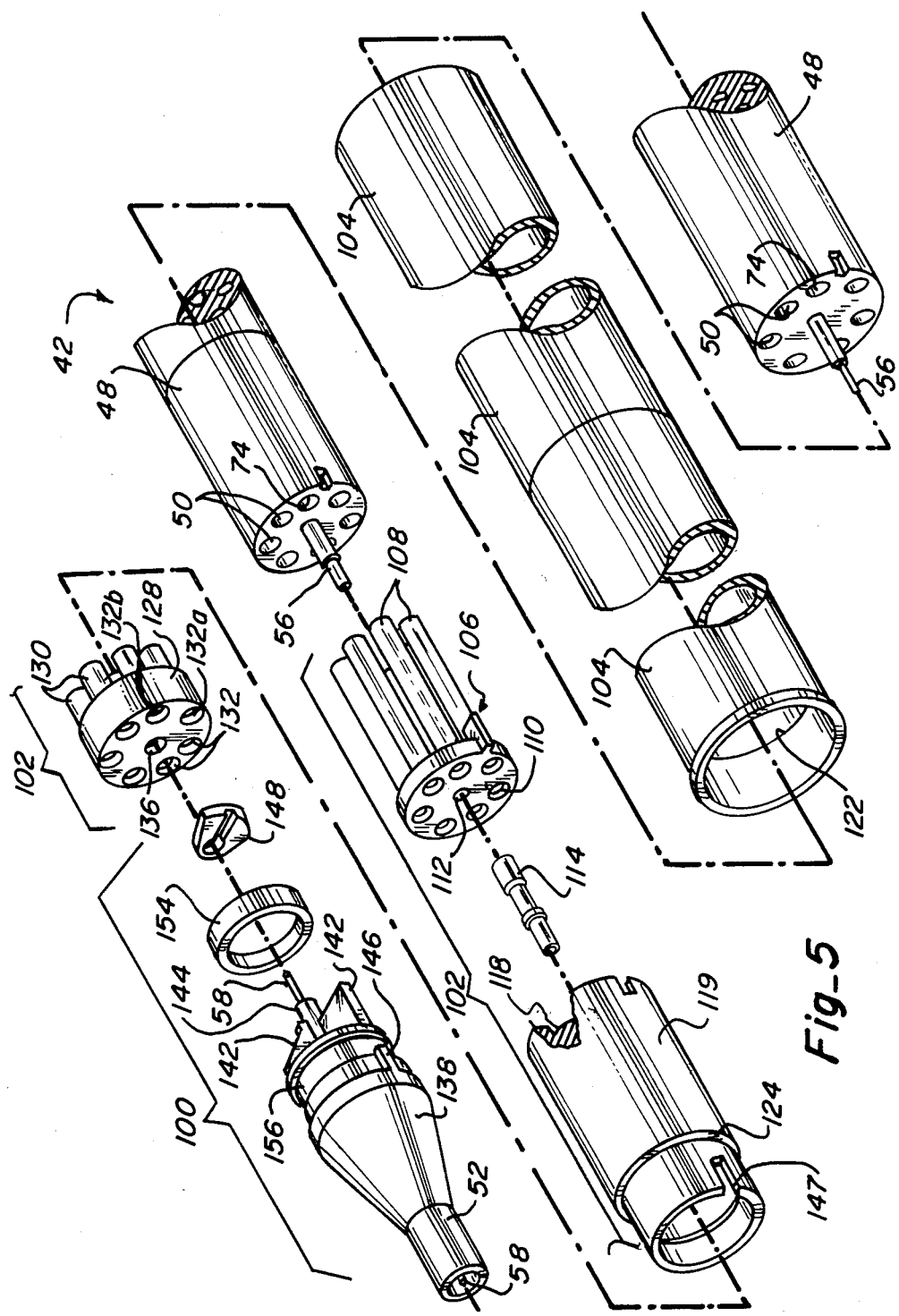

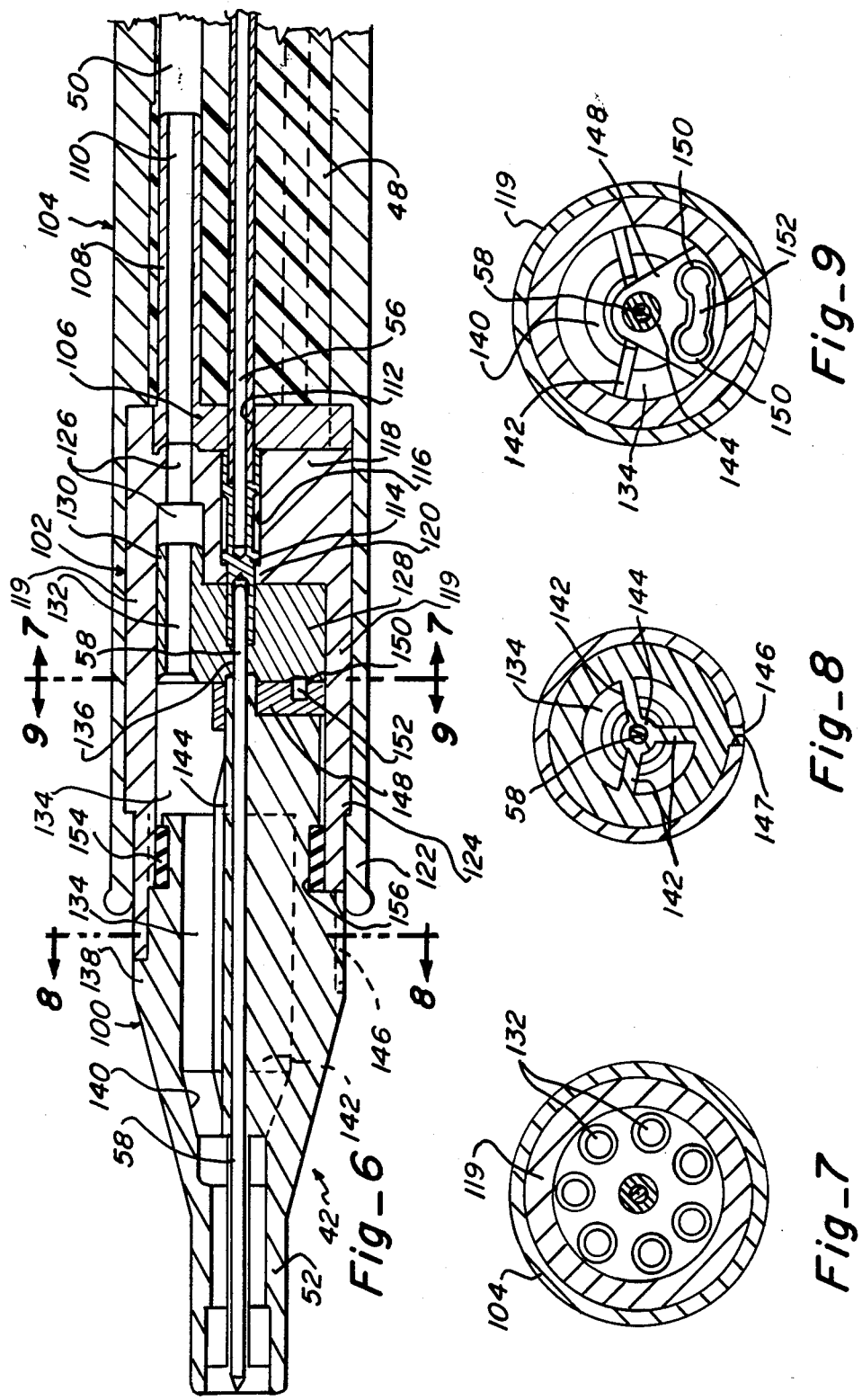

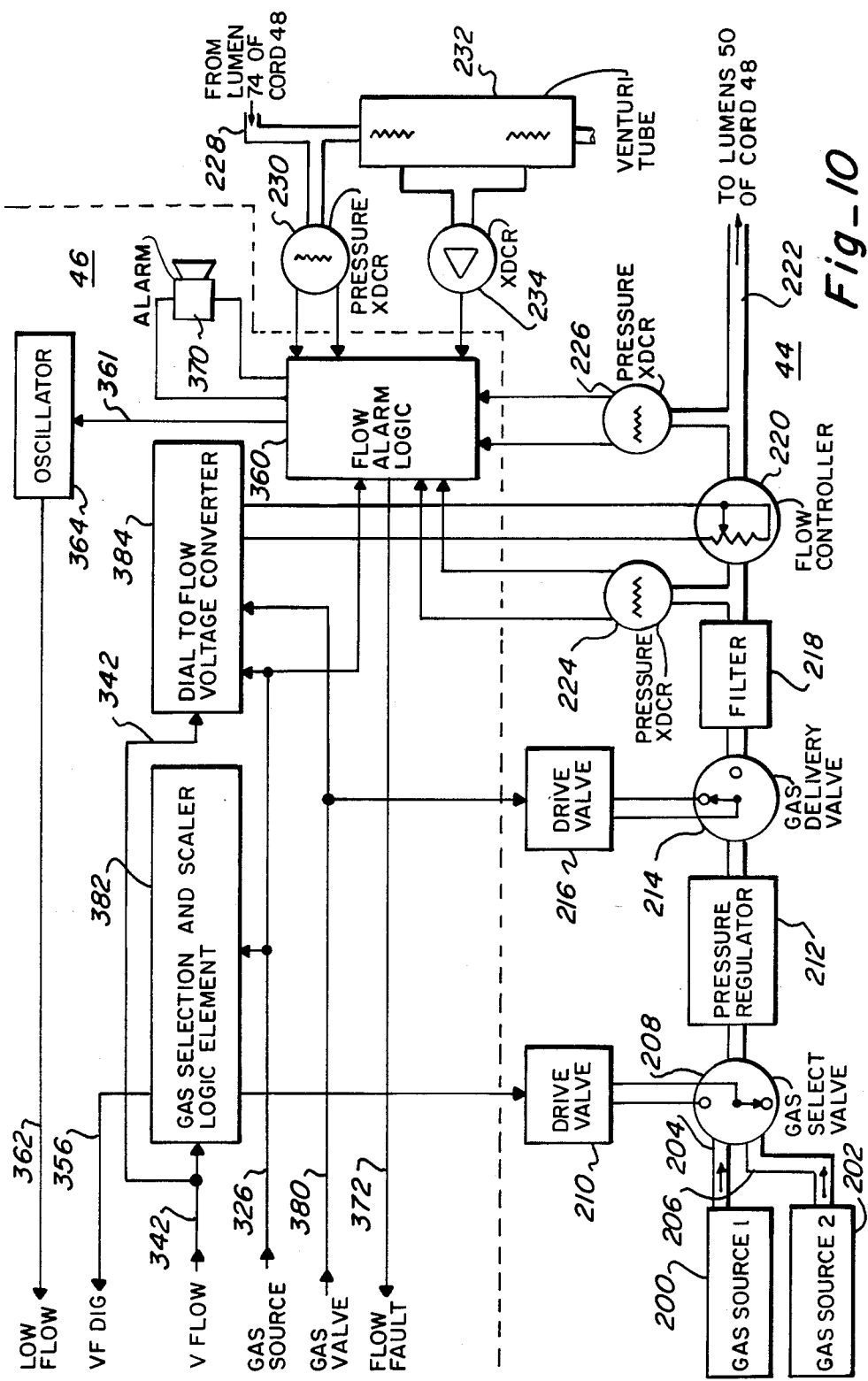
Fig_10

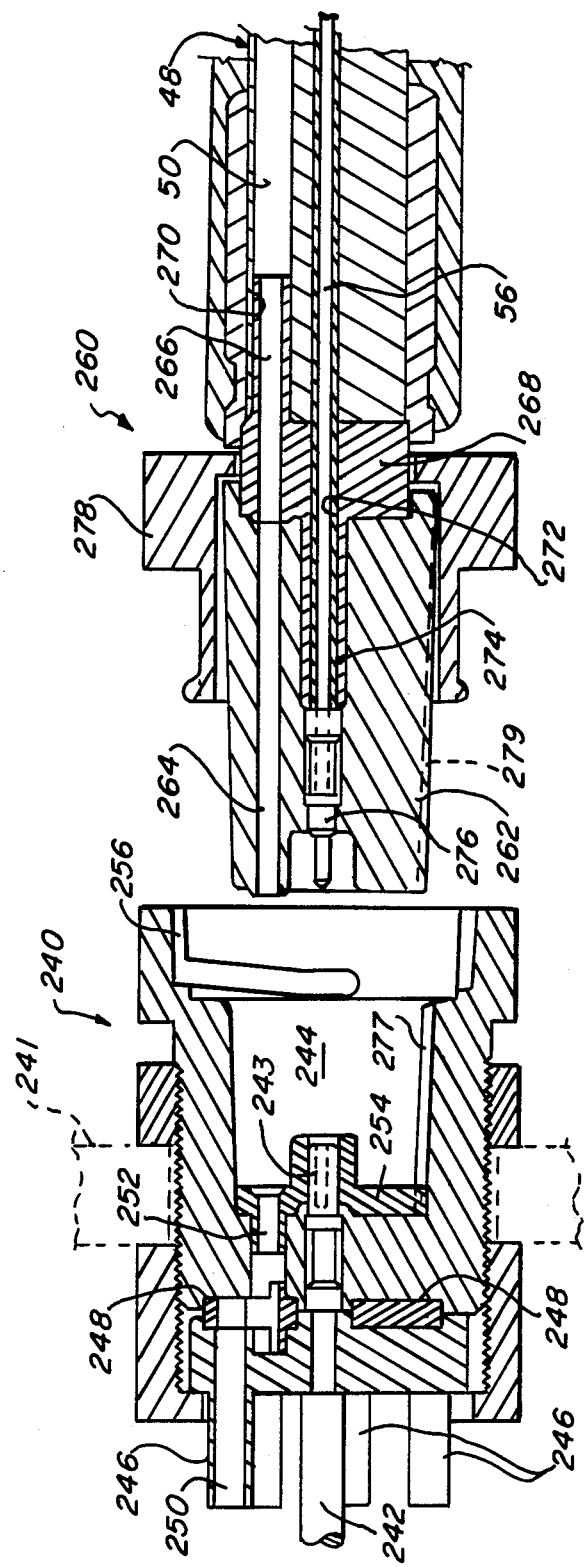
Fig_11B
Fig_11A

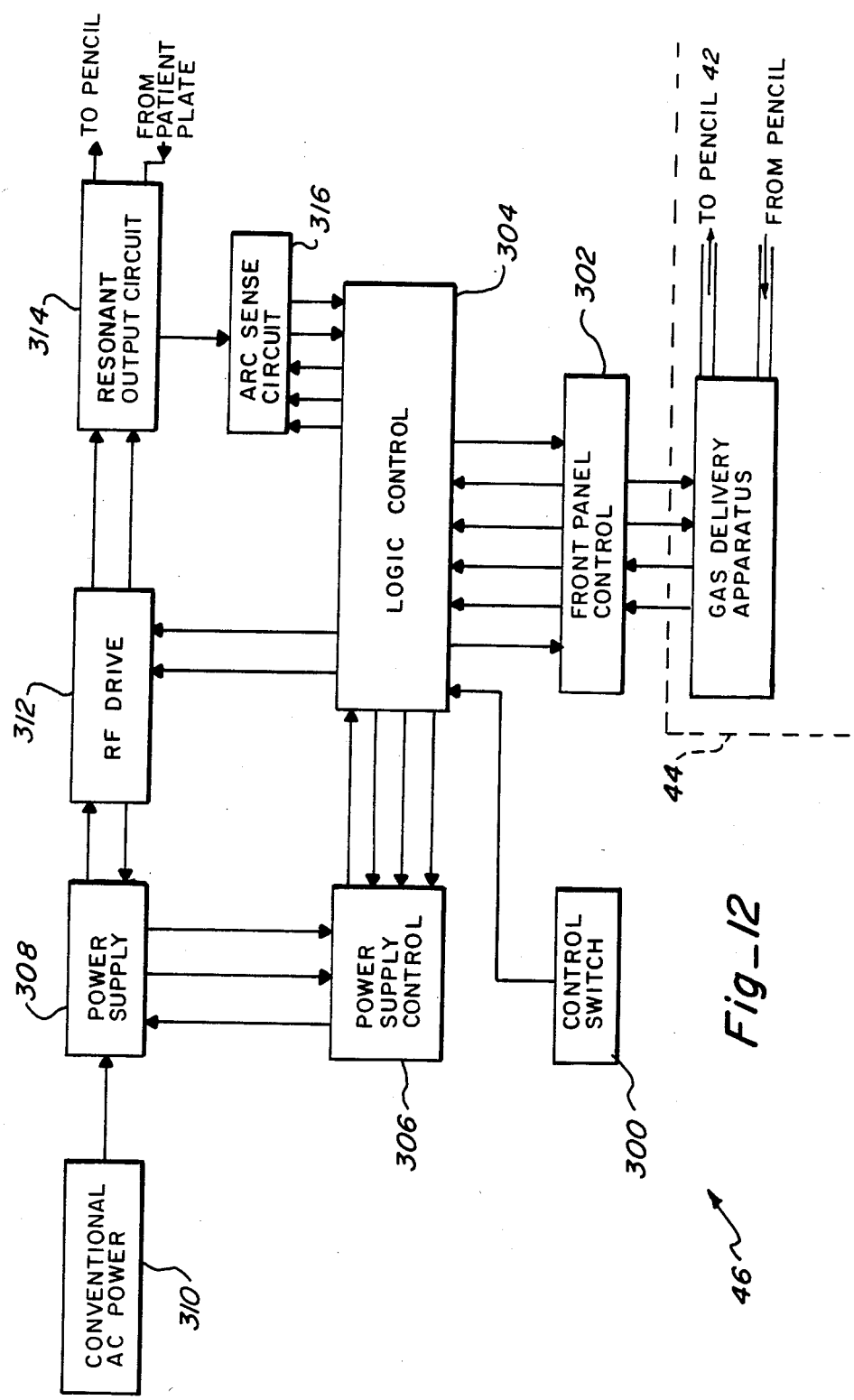
Fig_12

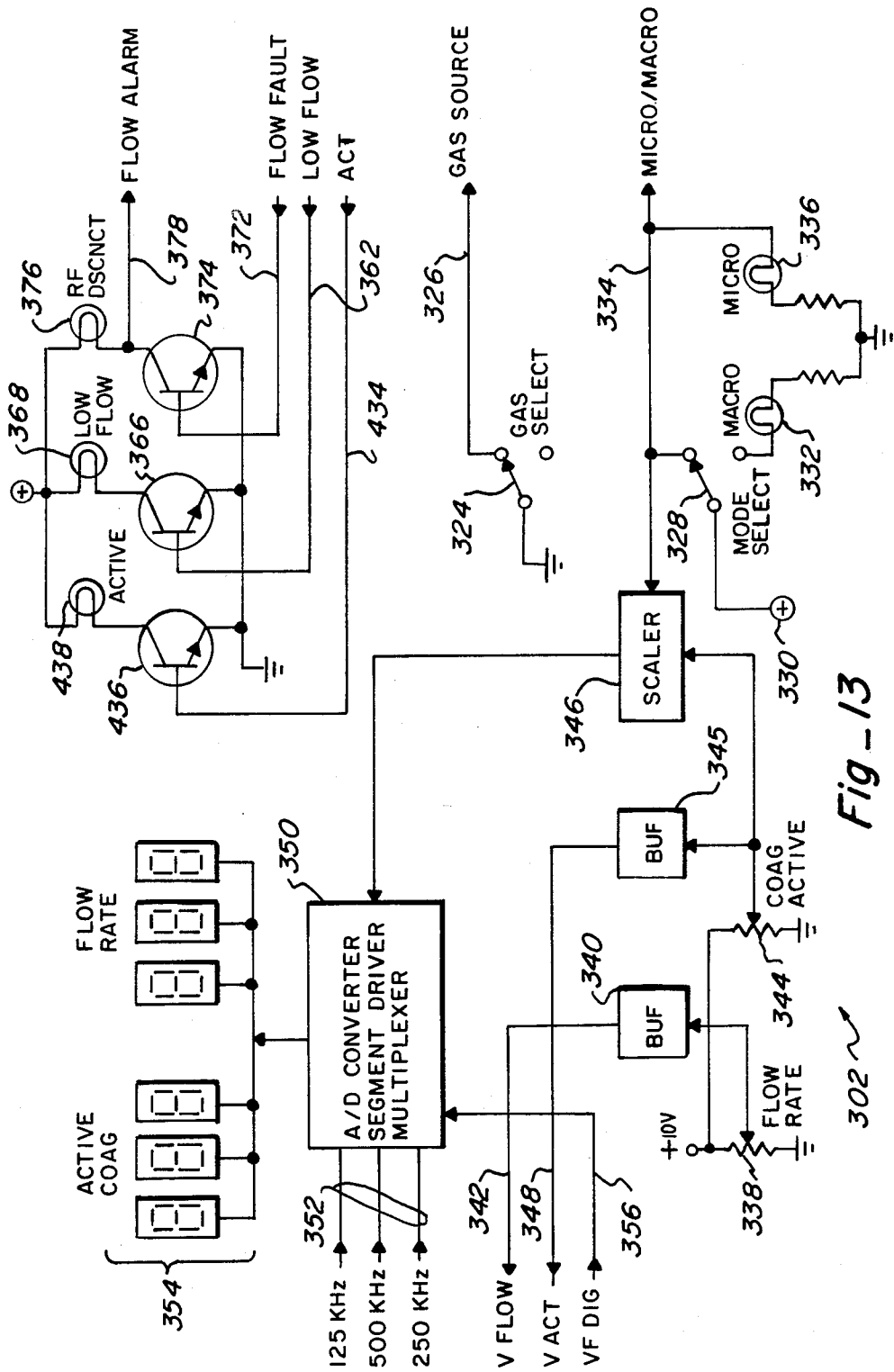
Fig_13

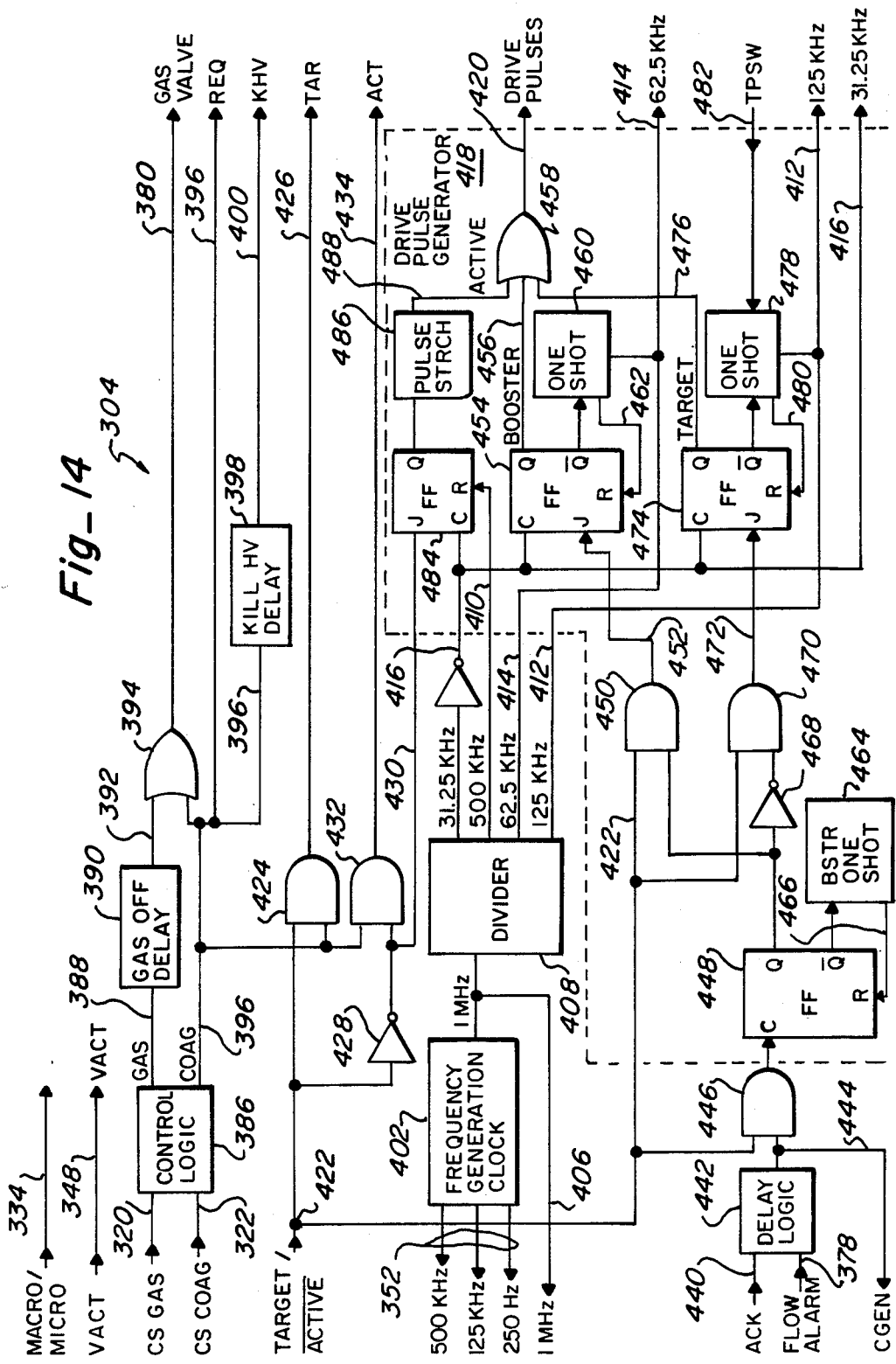
Fig_14

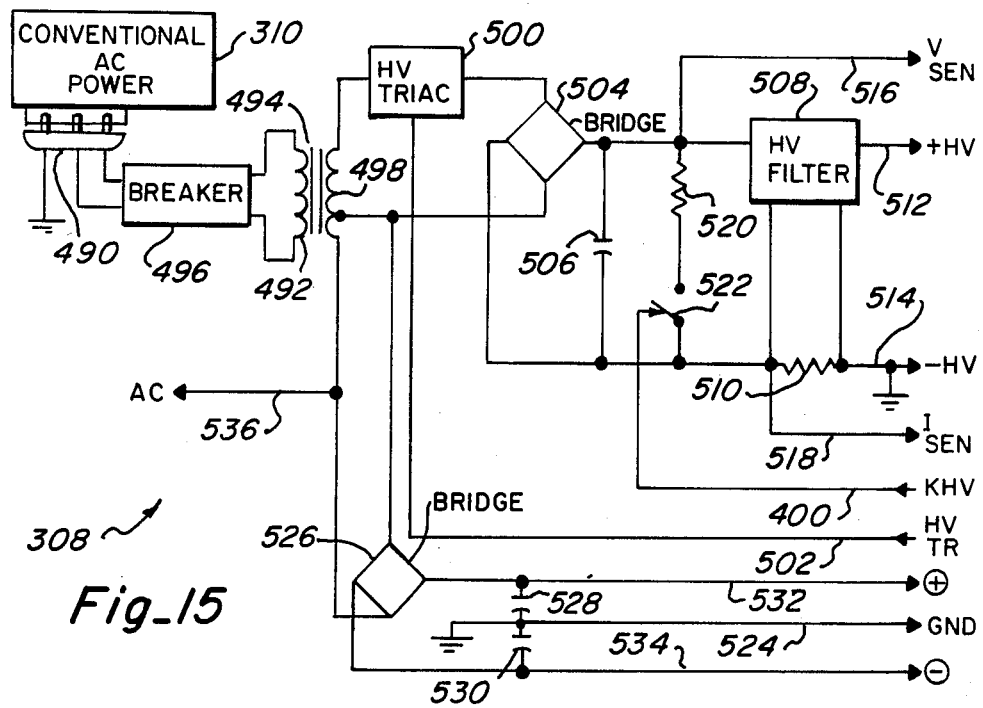
Fig_15
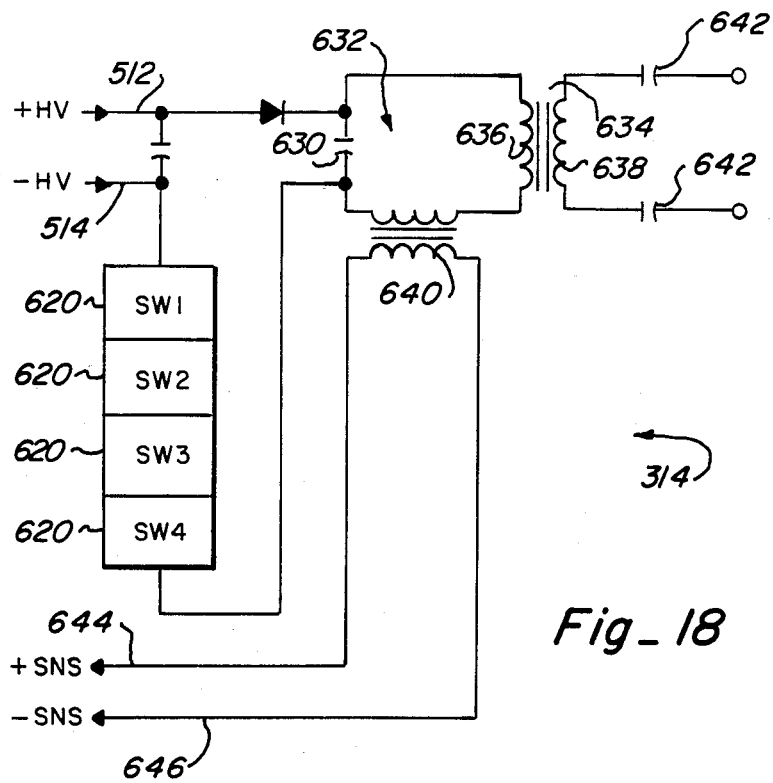
Fig_18

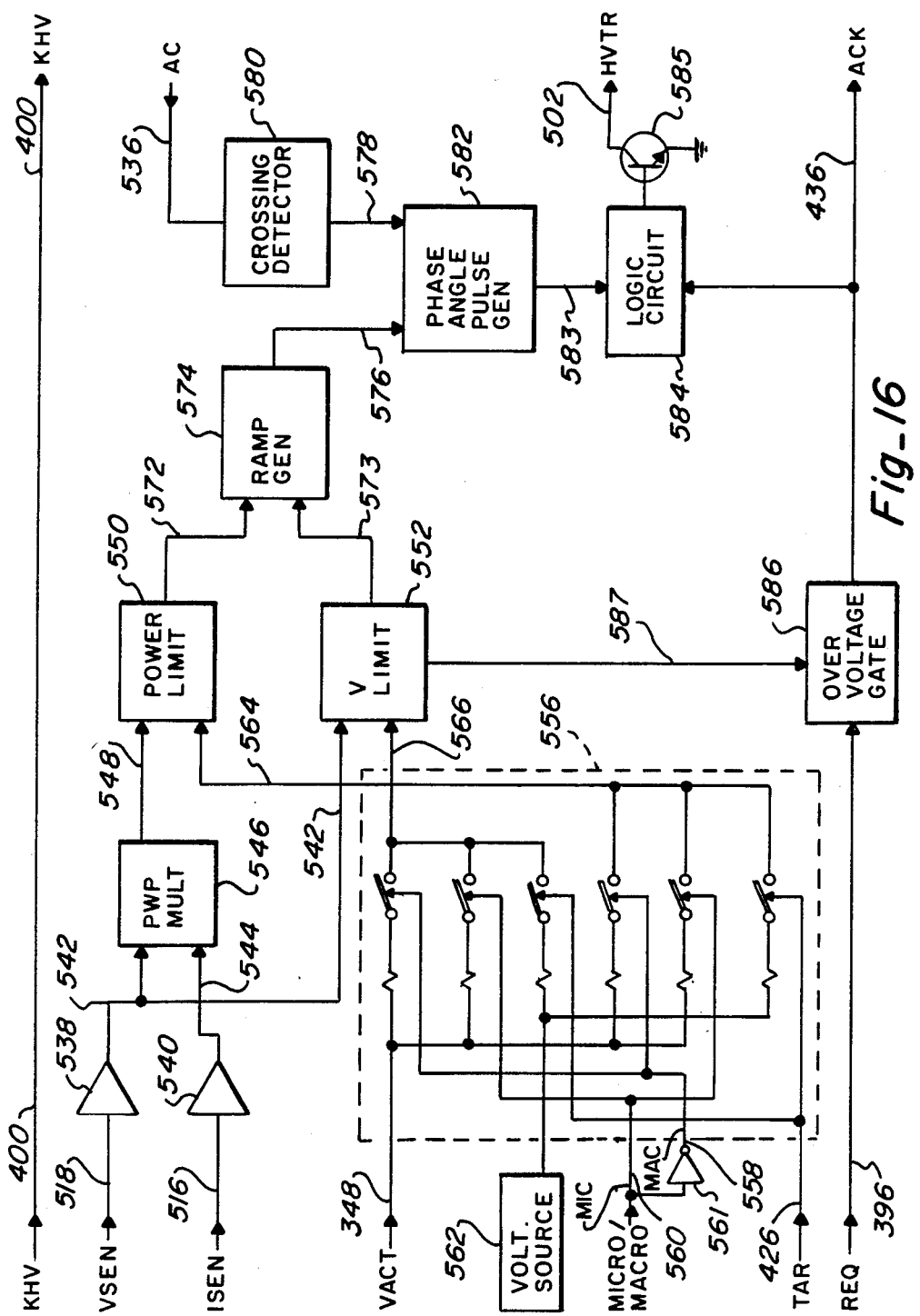
Fig_16

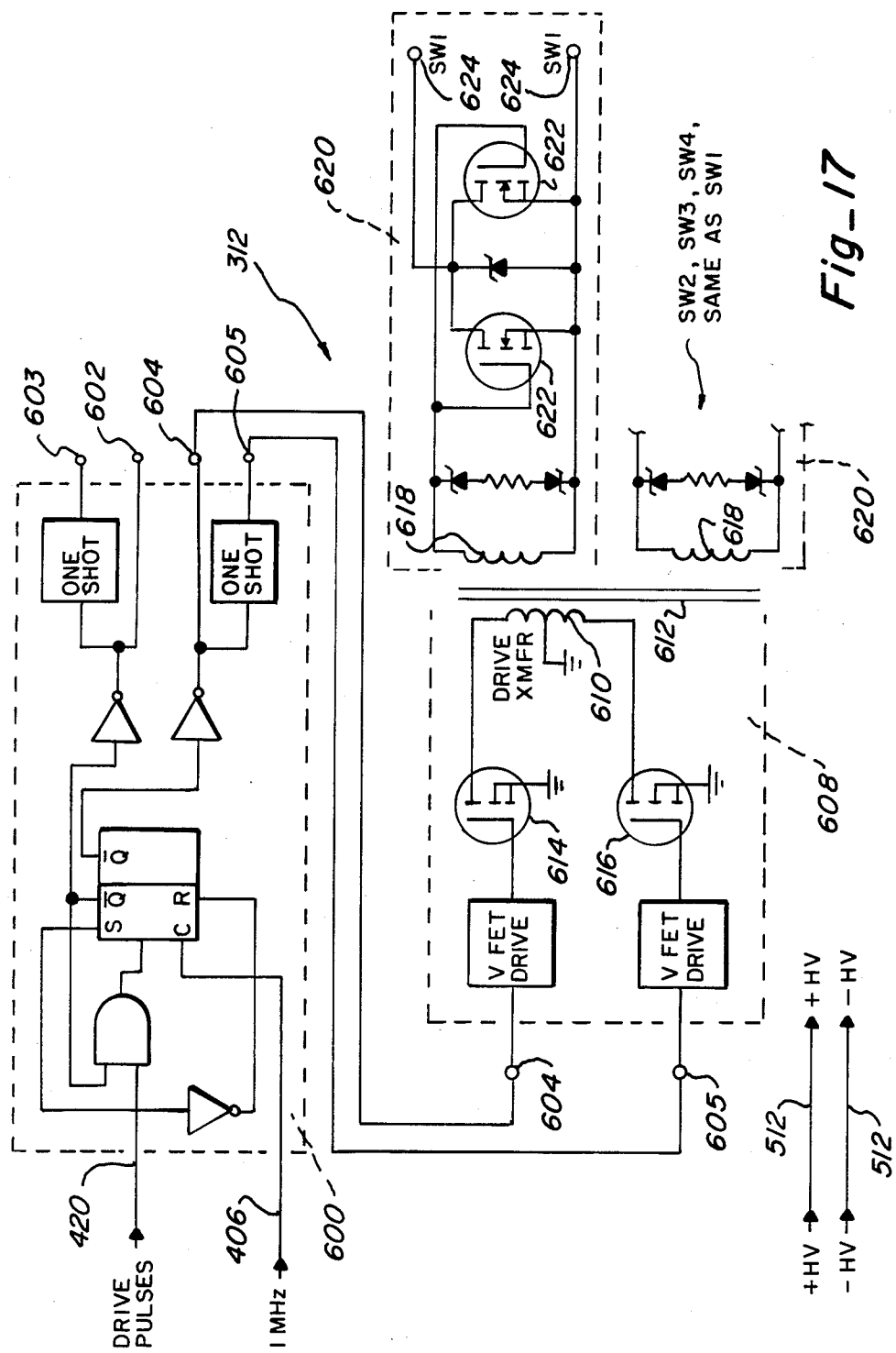
Fig_17

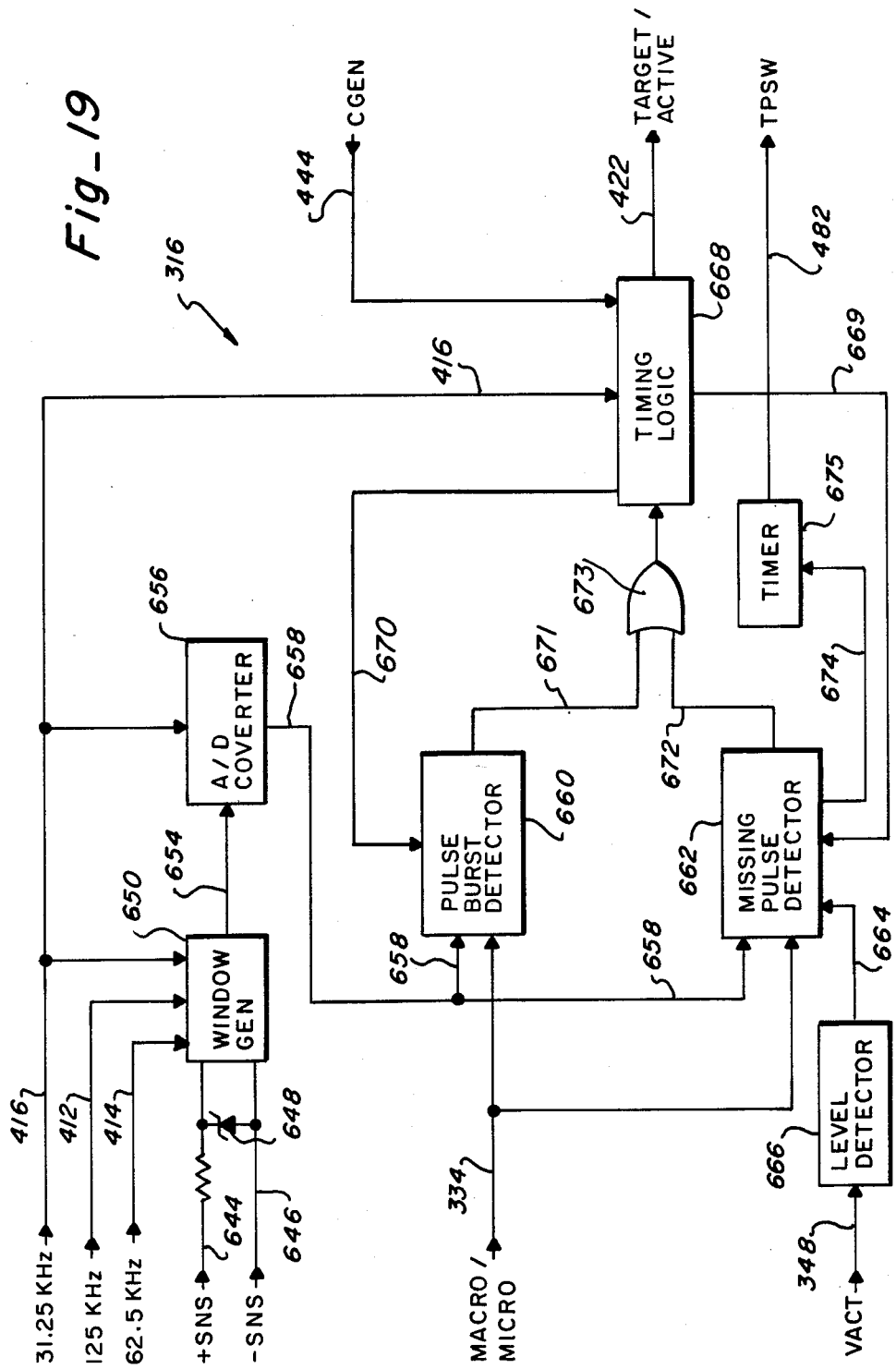

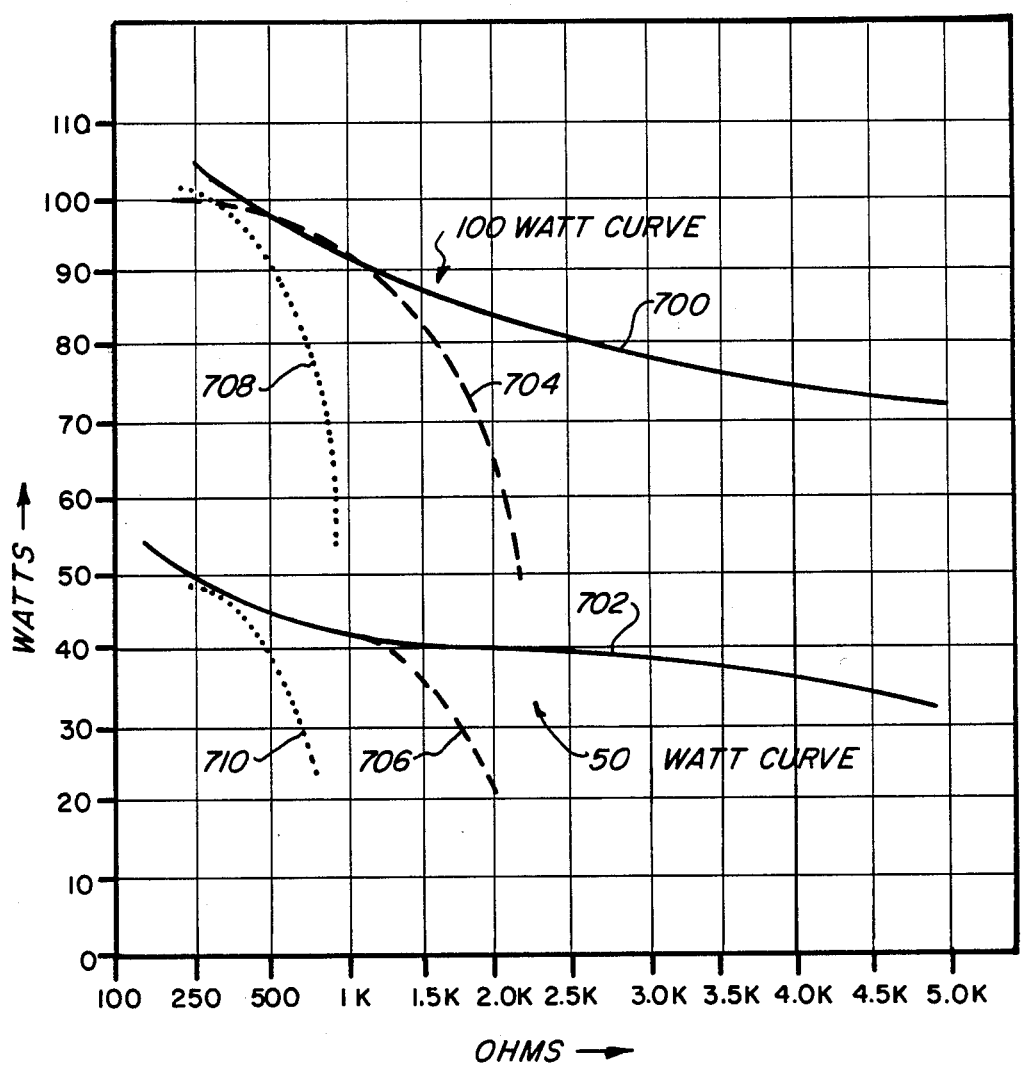
Fig_20

Fig_23A

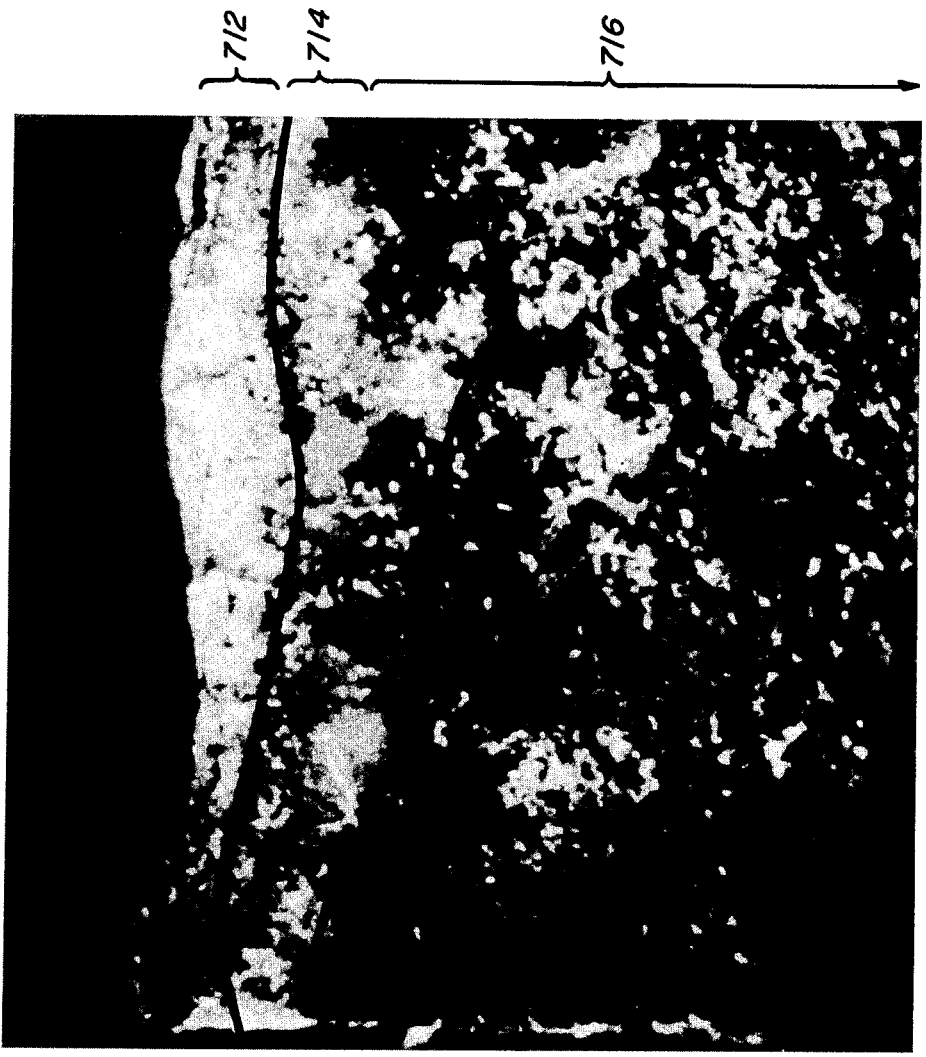
Fig_23B

ELECTROSURGICAL CONDUCTIVE GAS STREAM TECHNIQUE OF ACHIEVING IMPROVED ESCHAR FOR COAGULATION

This invention relates to electrosurgery, and more particularly to a new and improved electrosurgical technique for achieving coagulation or a hemostatic effect, i.e. fulguration and desiccation, by conducting radio frequency (RF) electrical energy through a conductive inert gas stream to the tissue. In addition, the present invention relates to an electrosurgical fulguration arcing technique of creating an eschar and tissue effects offering a substantially improved capability for coagulation. Further still, the present invention relates to an electrosurgical non-arcing desiccation technique of applying electrical energy to tissue to achieve superior thermal desiccative effects.

BACKGROUND OF THE INVENTION

Electrosurgery involves the application of radio frequency electrical energy to tissue. The electrical energy originates from an electrosurgical generator (ESG) and is applied by an active electrode to the tissue. The active electrode typically has a small cross-sectional or limited surface area to concentrate the electrical energy at the surgical site. An inactive return electrode or patient plate contacts the patient at a remote location from the surgical site to complete the circuit through the tissue to the ESG. The patient plate is relatively large in size to avoid destructive energy concentrations. Alternatively, a pair of active electrodes may be used in a "bipolar" mode in which the electrosurgical energy flows directly through the tissue between the two active electrodes, and the electrosurgical effects are confined to the tissue directly located between the two closely-spaced electrodes.

A variety of different electrosurgical effects can be achieved, depending primarily on the characteristics of the electrical energy delivered from the ESG. Among the effects are a pure cutting effect, a combined cutting and hemostasis effect, a fulguration effect and a desiccation effect. Desiccation and fulguration are usually described collectively as coagulation. Many conventional ESG's offer the capability to selectively change the energy delivery characteristics and thus change the electrosurgical effects created.

Satisfactory fulguration effects have been particularly difficult to obtain. Some surgeons have preferred to use older spark gap generators known as "Bovie" devices for fulguration, but use other more modern ESG's for cutting or cutting with hemostasis. Indeed, spark gap ESG's have been the standard against which modern solid state ESG's have been measured for achievement of satisfactory fulguration effects. One modern ESG which achieves substantially improved fulguration effects, compared to both spark gap and previous solid state ESG's is described in U.S. Pat. No. 4,429,694, assigned to the assignee hereof. Despite the improvements available in fulguration, certain disadvantages remain for which there have been no satisfactory alternatives.

Conventional fulguration is characterized by electrical arcing through the air from various locations on the metal surface of the active electrode, with the arcs contacting the tissue in somewhat of a random non-predictable manner. In many cases, arcs leave the active electrode in an initial trajectory traveling away from the tissue before actually curving around and striking the tissue surface. The result is an uneven, randomly concentrated or distributed delivery of arcing energy. An uneven eschar of variable characteristics is created on the surface of the tissue, as is exemplified by the eschar shown in FIGS. 1, 2, 3A and 3B. The characteristics of the prior art eschar have been studied as a part of the present invention. Even though such characteristics have probably existed for some considerable time, and therefore are prior art, the development of the present invention has resulted in what is believed to be the first relatively complete understanding of the prior art eschar and the practical coagulation or hemostatic consequences of it.

The random delivery of the arc energy creates holes which are significantly disparate in diameter (or cross-sectional size) and in depth, as is shown in FIGS. 1, 2, 3A and 3B. The larger, deeper holes are formed by repeated arcs contacting the tissue at approximately the same location. The smaller arc holes are also present in the tissue but they are unevenly distributed about the larger arc holes. The smaller arc holes are created by single individual arcs, or the less repetitious arcing to the tissue at the same location. The smaller arc holes are relatively small in diameter or cross-section and relatively shallow in depth, compared to the larger arc holes. Significant variations in cross-sectional size and depth between the large and small arc holes occur. Significant variations exist in the spacing and in the amounts of tissue between the large and small arc holes, causing the substantial variations in the surface distribution of the holes.

Thermal necrosis occurs in the tissue between the arc holes. The degree of thermal necrosis varies between total carbonization between the more closely spaced larger holes, to necrosis without charring or carbonization between the more widely separated smaller arc holes.

The eschar created has two distinct layers above the unaffected viable tissue. An arc hole reticulum of the tissue subjected to necrosis is created by the pattern of arc holes, and this arc hole reticulum extends to a depth or layer referenced 30 as shown in FIGS. 3A and 3B. The arc hole reticulum 30 extends to greater depths in the areas of the deeper arc holes, and to substantially shallower depths in the areas of the shallower arc holes. Due to the random distribution and depth of the arc holes, the arc hole reticulum is relatively uneven in depth. Significant variations in the depth of the arc hole reticulum layer are typical. A layer 32 of thermally desiccated tissue is located below the arc hole reticulum layer 30. Tissue necrosis in the layer 32 occurs as a result of desiccation due to the current heating effects of the electrical energy dissipating from the arcs. The desiccation layer 32 is also uneven in depth and location due to the nonuniform application of the arcing energy over the arc hole reticulum layer 30. Significant variations in the depths of the desiccation layer are also typical.

Over a given area of tissue, certain locations such as those shown on the right hand side in FIG. 3A are only moderately affected by the arcing energy. A thin arc hole reticulum and a thin desiccation layer result. Other areas, such as those shown on the left hand side of FIG. 3B, have a relatively thick eschar formed therein. Very thick carbonized eschars tend to be fragile and are prone to crack when flexed, usually resulting in renewed bleeding from the unaffected tissue at 34 below the desiccation layer. Thin eschars are more flexibile and therefore more desirable, but it has been difficult to obtain sufficient coagulation effects from thin eschars.

Causes of the uneven eschar created by prior fulguration techniques are not known with certainty, but numerous factors are theorized to play a role. One of the more significant contributory factors is probably changes in impedance in the arc pathway between the active electrode and the tissue. Impedance changes may result from variations in the distance which the arcs travel through the air, due to the changes in ionization potential between the active electrode and the tissue. It is virtually impossible for the surgeon to maintain the active electrode at a consistent distance from the tissue, particularly if the tissue is moving due to pulsation, or due to puckering and swelling as a result of applying the electrical energy. The arcing from random locations on the active electrode also creates different arc length pathways and hence impedances. The combined impedance of the tissue and the eschar changes with the application of electrical energy. The volatilization of the cells and vaporization of the moisture in the cells changes the relative impedance in a localized spot-to-spot manner on the surface of the tissue. The formation of the charred material also influences the arc pathways, presenting an opportunity for subsequent arcs to return to the tissue at the same location and thereby enlarge the pre-existing arc hole and create even further charring.

Another problem with conventional electrosurgery is that it is very difficult if not impossible to achieve effective fulguration on spongy or vascular tissue such as the liver or the spleen, or on other tissues from which there is a tendency for blood to continually ooze over the surface from the highly developed vascular network within the tissue. Often, only the surface of the oozing blood is coagulated, with no penetration to the surface of the tissue below the layer of blood. A superficial coagulum results on the surface of the blood, but this coagulum quickly sloughs away resulting in only temporary hemostasis. Of course, once the temporary coagulum sloughs away, bleeding continues. Even if a coagulation effect on the tissue surface can be established, it is easily destroyed or perforated by the arcs returning to the same locations causing the longer, deeper arc holes. The deeper arc holes perforate the eschar and extend into the viable tissue below the eschar to provide a pathway for continued bleeding. The heat created by the arcs causes boiling of moisture below the eschar, and the pressure of resulting vapor can also rupture the eschar to reinitiate bleeding.

Apart from the tissue disadvantages of conventional electrosurgical fulguration, certain other practical problems exist. Arcing from the active electrode rapidly increases the temperature of the active electrode. Electrode heating is responsible for a number of problems. If the heated active electrode contacts the tissue, as it inevitably will, or if the active electrode is immersed in fluid such as blood, proteins from the tissue or the blood are denatured and stick to the active surface of the electrode. The buildup of charred material on the electrode eventually creates a sufficiently high impedance so that adequate power can no longer be delivered. The surgeon must continually clean the electrode by wiping or scraping the charred material, which disrupts, distracts, and prolongs the surgical operation. Freshly created eschars can be detached in an effort to free a sticking electrode from the tissue surface. The random accumulation of charred material on the active electrode creates more random delivery of the arcing energy, even further increasing the random delivery pattern. Because of the variable nature of the impedance of the charred material, consistent power application is difficult or impossible. The accumulation of the charred material can obscure the surgeons view of the surgical site. The temperature of the active electrode may reach sufficiently elevated levels to transfer molten metal from the electrode to the patient, creating questionable effects. Because the electrode contacts the tissue, there is a potential for cross-contamination between viable tissues and diseased tissues. Although the clinical problems associated with cross contamination are not fully understood at the present time, the advantages of eliminating the possibility are evident. A significant smoke plume also results from the burning tissue because of the air environment in which the electrosurgery occurs. Not only does the plume produce a noxious odor, but there may be some evidence that particulates in the smoke plume from burning tissue may contain hazardous chemicals, virus, bacteria, neoplastic cells and other hazards. Of course, the oxygen environment in which the electrosurgy is conventionally conducted exhibits a potential for igniting paper drapes, surgical sponges and the like.

Some of the typical problems associated with creating and applying the arcs in conventional electrosurgery can be improved by optimizing the operating and other characteristics of the electrosurgical generator. U.S. Pat. No. 4,429,694 discloses an improved ESG which reduces some of the described disadvantages during fulguration. However, many of the disadvantages cannot be avoided and many of the characteristics cannot be improved by conventional electrosurgical techniques and equipment, due to the limitations previously inherent in electrosurgery.

The conventional technique of obtaining thermal desiccation by use of a conventional ESG is to apply electrical energy from a flat surface of the active electrode placed in contact with the tissue. An electrical resistance heating effect is created by the current flowing into the tissue from the active electrode. Because the active electrode contacts the tissue surface over a relatively large area, no arcing is intended to occur. To spread the thermal desiccation effect over a substantially large area, the active electrode is moved from location to location. It is very difficult to apply a level of energy which will obtain thermal desiccation but which will not cause the tissue to stick on the flat surface of the active electrode or arcing from the active electrode to non-contacted surface areas. The thermal desiccation effects are unevenly distributed because the active electrode is moved from spot to spot. Overlapping the spots of energy application can enhance the probability for tissue sticking and exaggerate the variable depth effects. Of course, moving the active electrode from spot to spot is very time consuming in an operation where time is very important or critical.

The prior art desiccation technique can only be applied to create surface desiccation effects. Furthermore, the inability to accurately control the amount of power, tissue sticking effects, and the like have prevented the prior use of electrosurgery on very thin fragile tissue such as the mesentary, and in other surgical techniques.

It is against this abbreviated background of previously existing disadvantages and problems in electrosurgery that the advantages and improvements of the present invention can be better appreciated.

BRIEF SUMMARY OF THE INVENTION

In general, the electrosurgical technique of achieving coagulation in accordance with the present invention involves conducting a predetermined ionizable gas in a directed or generally laminar jet to the tissue at a predetermined flow rate sufficient to clear natural fluids from the tissue and to substantially expose the underlying tissue, while simultaneously conducting electrical energy at a predetermined primary radio frequency range in the gas jet through ionized conductive pathways. To achieve fulguration, the electrical energy is conducted as arcs in the ionized pathways. To achieve desiccation, the electrical energy is conducted in the ionized pathways as a non-arcing diffuse current.

The eschar resulting from fulguration is substantially improved compared to the eschar created by typical prior electrosurgical fulguration which achieves the same hemostatic or coagulation effect. The fulguration eschar created by the present invention is characterized by an outer generally uniform depth reticulum of arc-created holes penetrating the tissue from a surface of the eschar; arc holes which are smaller in size, greater in number, more comparable or uniform in cross-sectional size, and substantially more uniformly spacially distributed over the surface of the eschar; and a greater wall thickness of tissue between adjacent arc holes which provides pliability without cracking. Below the arc hole reticulum there exists a generally uniform-depth thermally desiccated layer which separates the arc hole reticulum from the unaffected tissue. The thermal desiccation layer of the fulguration eschar available from the present invention is also shallower in depth compared to the thermal desiccation layer of an eschar created by prior fulguration techniques. In addition, the fulguration eschar created by the present invention is further characterized by a substantial absence of charring and carbonization in the arc hole reticulum.

The smaller sized, shallower, more evenly distributed arc holes more effectively activate coagulation in the blood and provide the necessary reticulum structure for supporting the coagulum. The shallower depth of both the arc hole reticulum and the thermal desiccation layer achieve greater flexibility and pliability of the eschar and a comparable decrease in the possibility for cracking which would result in renewed bleeding. The more uniform depth of the fulguration eschar also achieves more effective coagulation and tissue effects over the surface of the tissue. The shallower depth of the fulguration eschar resulting from practicing the present invention causes less tissue destruction while still achieving improved coagulation.

The desiccation coagulation of the present invention is believed to be a totally new electrosurgical effect and results in the creation of a desiccation eschar characterized by a single layer of tissue which has been subjected to thermal necrosis and desiccation to the extent where it substantially seals the underlying unaffected tissue. Compared to prior techniques of thermal desiccation coagulation, the thermally desiccated layer of the eschar obtained from the present invention is relatively thin and uniform in depth. It is characterized by an absence of perforations created by the electrical energy. The coupling effect of the diffuse non-arcing current to the tissue is gentle, allowing the desiccation technique of the present invention to be applied in surgical procedures where electrosurgery has not been previously successfully applied, such as on thin tissue such as the mesentery and in microsurgical applications.

The flow rate of the gas jet should be sufficient to clear fluids from the tissue so that the eschar can be formed in the stroma or supporting structure of the tissue, as opposed to on top of the fluid covering the tissue. To create satisfactory eschar characteristics and obtain good operation of the present invenion, an electrosurgical generator which supplies electrical energy to the gas jet should have a relatively broad internal impedance characteristic. The impedance characteristic should result in the transfer of sufficient power into fluids or fluid-perfused tissue on the low end of the generator impedance curve, even though the gas jet will normally clear the fluids from the tissue surface. The impedance characteristic should also result in the transfer of sufficient power on the high end of the generator impedance curve to ionize the gas flowing at the predetermined flow rate when the gas jet is sufficiently spaced from the tissue to avoid any operative effect on the tissue. In general, the high end of the impedance transfer characteristic of the generator should extend approximately two to three times beyond the typical high end impedance range of a prior art solid state electrosurgical fulguration device.

Many other significant features are inherent in the present invention, as well as many improvements over prior art coagulation techniques. These various features and improvements are discussed more completely in the following detailed description of the preferred embodiment taken in conjunction with the drawings.

BRIEF DESCRIPTION OF THE DRAWINGS

FIG. 1 is an enlarged top view photograph of canine liver tissue fulgurated by a conventional prior art electrosurgical unit utilizing the invention disclosed in U.S. Pat. No. 4,429,694, illustrating coagulative effects created on tissue by what is believed to be the best previous prior part electrosurgical fulguration technique.

FIG. 2 is an enlarged top view photograph of bovine liver tissue fulgurated by a conventional prior art electrosurgical unit utilizing the invention disclosed in U.S. Pat. No. 4,429,694, illustrating coagulative effects created on tissue by what is believed to be the best previous prior part electrosurgical fulguration technique, with a thin layer of the tissue illustrated in a backlighted condition.

FIGS. 3A and 3B are enlarged photographs of cross sections of canine liver tissue similar to but not the same as that shown in FIG. 1 which has been fulgurated similarly as that shown in FIG. 1, taken at respectively different locations from a single piece of tissue, and illustrating by lines marked thereon the depth of different coagulative effects from the surface of the tissue.

FIG. 4 is a generalized schematic view of an electrosurgical unit (ESU) embodying the present invention, illustrating an electrosurgical generator (ESG), a gas delivery apparatus, a pencil, and a segment of tissue shown illustratively in cross section.

FIG. 5 is an exploded view of the major components of an actual embodiment of the pencil shown generally in FIG. 4.

FIG. 6 is a section view taken along an axis of the forward portion of a pencil assembled from the elements shown in FIG. 5.

FIG. 7 is a section view taken substantially in the plane of line 7—7 shown in FIG. 6.

FIG. 8 is a section view taken substantially in the plane of line 8—8 shown in FIG. 6.

FIG. 9 is a section view taken substantially in the plane of line 9—9 shown in FIG. 6.

FIG. 10 is a schematic and block diagram of the gas delivery apparatus shown in FIG. 4, and a block diagram of a portion of the ESG shown in FIG. 4 which operatively interacts with the gas delivery apparatus.

FIGS. 11A and 11B are, respectively, axial section views of a female connector and a male connector by which a cord leading to the pencil is operatively connected to the electrosurgical generator and gas delivery apparatus as shown in FIG. 4.

FIG. 12 is a block system diagram of the elements of the ESG and of the gas delivery apparatus shown in FIG. 4.

FIG. 13 is a block and schematic diagram of the Front Panel Control element of the ESG shown in FIG. 12.

FIG. 14 is a block and logic diagram of the Logic Control element of the ESG shown in FIG. 12.

FIG. 15 is a block and schematic diagram of the Power Supply element of the ESG shown in FIG. 12.

FIG. 16 is a block and logic diagram of the Power Supply Control element of the ESG shown in FIG. 12.

FIG. 17 is a block, logic and schematic diagram of the Radio Frequency or RF Drive element of the ESG shown in FIG. 12.

FIG. 18 is a block and schematic diagram of the Resonant Output Circuit element of the ESG shown in FIG. 12.

FIG. 19 is a block and logic diagram of the Arc Sense Circuit element of the ESG shown in FIG. 12.

FIG. 20 is a static load graph of power output versus non-inductive resistance loading which illustrates the impedance characteristics of the ESU of the present invention compared to two prior art ESGs.

FIGS. 23A and 23B are enlarged photographs of cross-sections of canine liver tissue similar to but not the same as that shown in FIG. 21 fulgurated similarly as that shown in FIG. 21, taken at respectively different locations from a single piece of tissue, and illustrating by lines marked thereon the depth of different coagulative effects from the surface of the tissue.

FIGS. 21, 22, 23A and 23B are intended to be comparable to FIGS. 1, 2, 3A and 3B respectively, and all are intended to be representative of the effects described.

FIGS. 24 and 25 are intended to be representative of the desiccation coagulation effects achieved by the present invention.

DESCRIPTION OF PREFERRED EMBODIMENT

Figure 3B:
Figure 21:
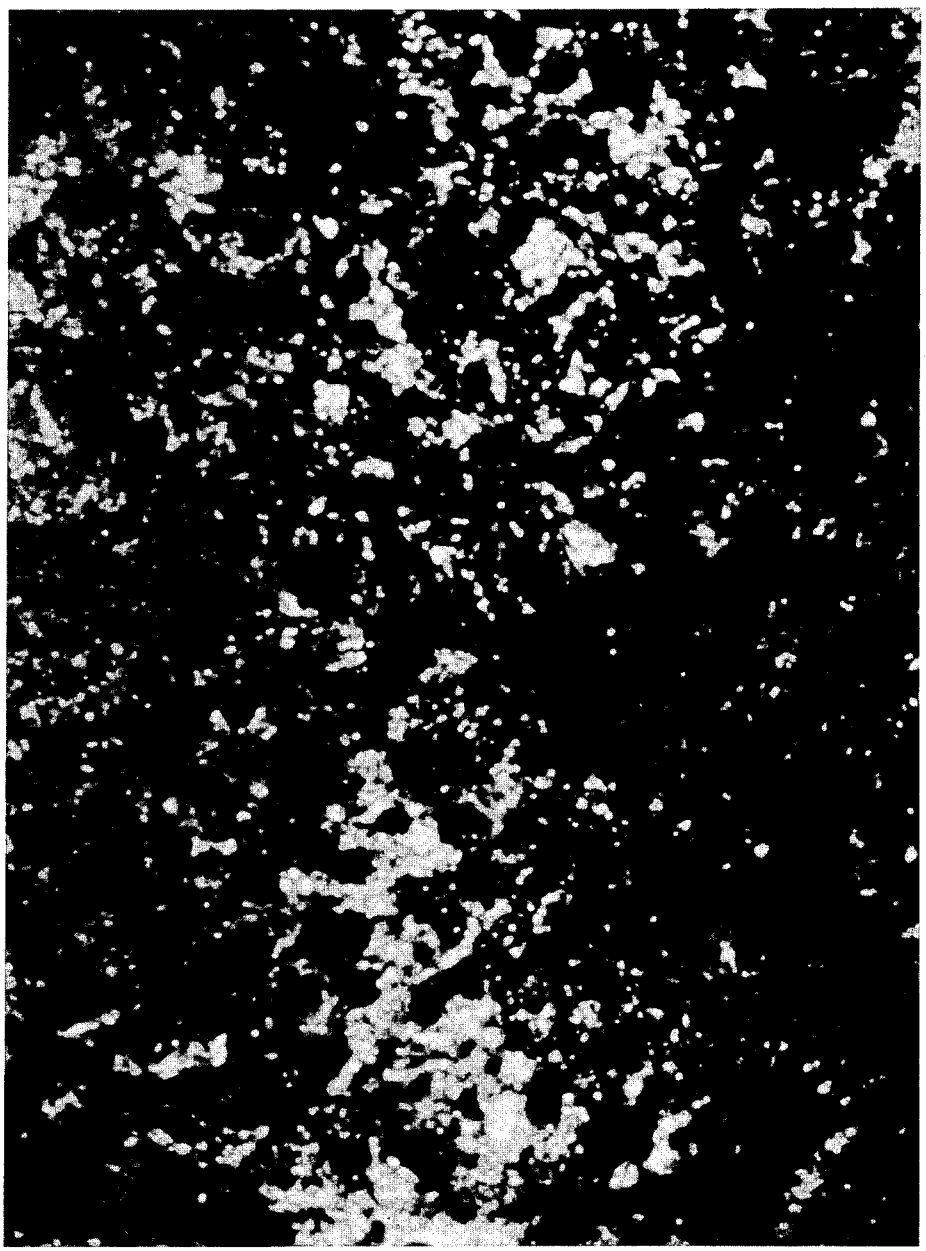
FIG. 21 is an enlarged top view photograph of canine liver tissue fulgurated by the ESU of the present invention and illustrating the improved fulguration coagulative effects available from the present invention.
Figure 22:
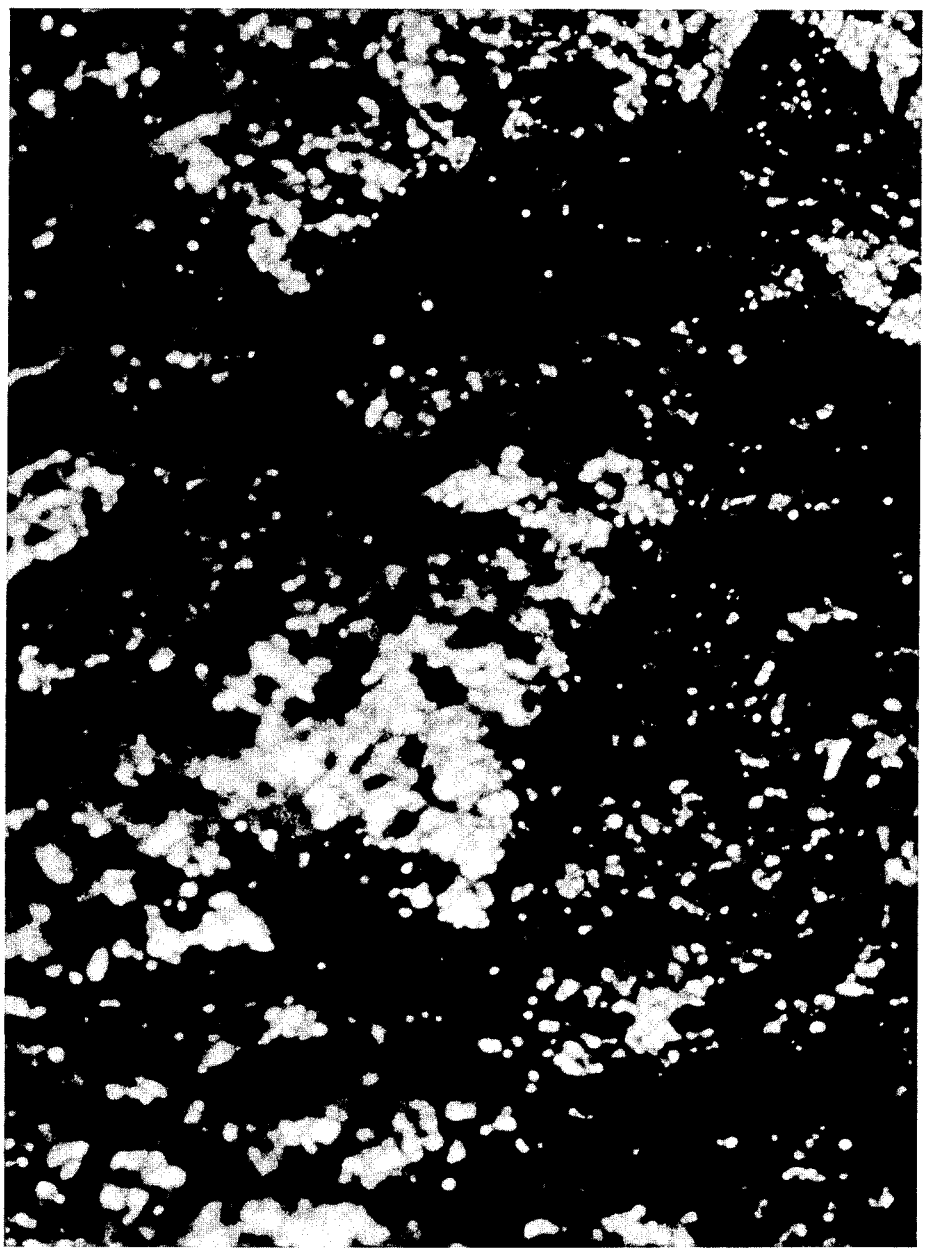
FIG. 22 is an enlarged top view photograph of bovine liver tissue fulgurated by the ESU of the present invention, with a thin layer of the tissue illustrated in a back lighted condition.

An electrosurgical unit (ESU) which embodies the present invention is shown generally in FIG. 4 and is referenced 40. The ESU 40 includes three major components, a pencil 42 which is manipulated by the surgeon, gas delivery apparatus 44 and an electrosurgical generator (ESG) 46. A flexible cord 48 connects the gas delivery apparatus 44 and the ESG 46 to the pencil 42. The gas delivery apparatus 44 delivers a predetermined gas through a plurality of individual passageways or lumens 50 in the cord 48 to the pencil 42. The gas issues from a nozzle 52 of the pencil 42 in a directed or substantially laminar flow stream or jet 54. The ESG 46 supplies electrical energy over a supply conductor 56 of the cord 48 to the pencil 42. The conductor 56 is electrically connected in the pencil to a needle-like electrode 58 which extends into the nozzle 52. The electrical energy supplied by the ESG 46 is of predetermined characteristic sufficient to ionize the gas flowing through the nozzle 52 and to create ionized pathways in the jet 54. The electrical energy travels in the ionized pathways in the jet 54 to a body tissue 62 where it creates a predetermined electrosurgical effect on the tissue 62.

In the fulguration mode of operation of the ESU, also referred to herein as a "macro" mode of operation, electrical energy is transferred in the ionized pathways in the form of arcs 60. The arcs 60 travel within the jet 54 until they reach the tissue 62 at the electrosurgical site. The jet 54 expands slightly above the surface of the tissue 62 and the arcs 60 disperse over a slightly enlarged area of the tissue surface compared to the cross-sectional area of the jet 54. The electrical energy of the arcs is transferred into the tissue 62 and creates the upper arc hole reticulum or layer 30 and a desiccated layer 32 therebelow. The arc hole reticulum 30 and the desiccated layer are schematically illustrated in FIG. 4, but are shown more in actuality in FIGS. 21, 22, 23A and 23B which are described in greater detail below.

Figure 24:
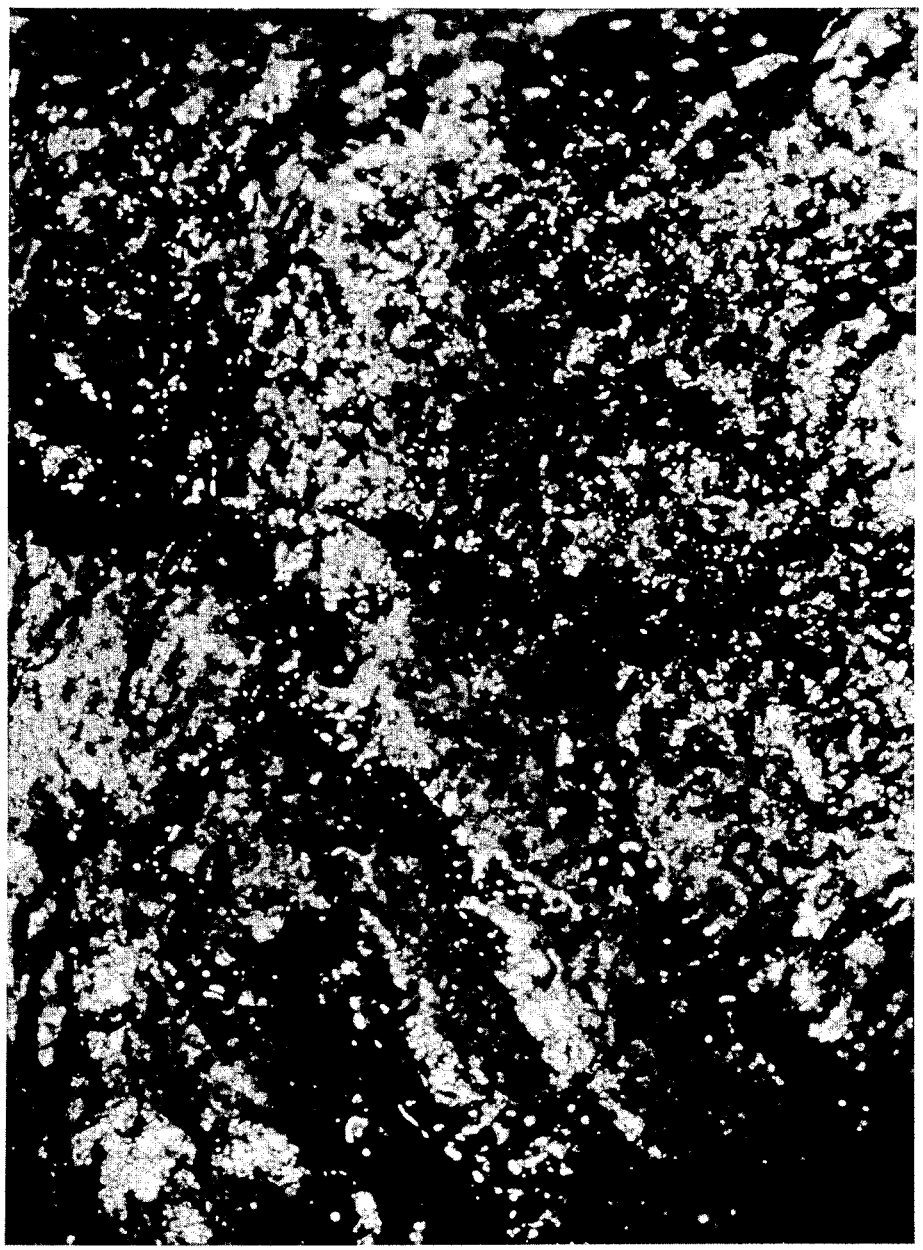
FIG. 24 is an enlarged top view photograph of a canine lung tissue which has been thermally desiccated by the ESU of the present invention over a major portion of the lung tissue illustrated.
Figure 25:
FIG. 25 is an enlarged photograph of a cross-section of rat liver tissue which has been desiccated by the ESU of the present invention and illustrating by a line marked thereon the depth of the coagulative desiccative effect relative to the surface of the tissue.

In the desiccation mode of operation of the ESU, also referred to herein as a "micro" mode of operation, the ionized pathways in the jet 54 transfer electrical energy from the electrode 58 as a non-arcing, conductive current. A gentle coupling effect is created at the tissue which does not cause holes in the tissue, because arcs are not present. As will be described more completely hereinafter, a desiccative electrosurgical effect is created, and only a desiccation layer similar to that schematically shown at 32 in FIG. 4 is formed on the surface of the tissue. The actual desiccative effects are shown by FIGS. 24 and 25 which are described in greater detail below. The normal unaffected tissue structure such as that at 34 exists below the surface desiccated layer 32. The jet expands slightly at the surface of the tissue to couple the non-arcing electrical current over a slightly enlarged area of the tissue surface compared to the cross sectional size of the jet. This type of desiccative coagulation electrosurgical effect has heretofore not been obtainable in the field of electrosurgery. The desiccative effects on the tissue offer the possibility of accomplishing substantially new and different types of electrosurgical procedures by use of an ESU.

The electrical energy delivered through the jet 54 travels through the tissue 62 to a return electrode or patient plate 70 which contacts the tissue 62. The patient plate 70 is connected by a return electrical conductor 72 to the ESG 46. A complete electrical circuit is thus established for conducting the energy from the ESG 46, to the pencil 42, through the jet 54, to and through the tissue 62, to patient plate 70, through the and return conductor 72 to the ESG 46.

To sense a proper operating condition within the pencil 42, a portion of the gas conducted to the pencil is returned in a sensing lumen 74 of the cord 48. The characteristics of the gas in the sensing lumen 74 are sensed by the gas delivery apparatus 44 to establish certain operating conditions before delivering the electrical energy over the supply conductor 56 to the pencil 42.

The details and importance in the present invention of the pencil 42, the gas delivery apparatus 44, the ESG 46, the characteristics of the jet 54 and the energy coupled in the jet, and the characteristics of the tissue effects and other resulting physiological consequences are described below.

Pencil

The pencil 42 is shown in FIGS. 5 and 6 as comprising a nozzle and electrode support assembly 100, a coupler assembly 102 and a handle 104. The cord 48 from the gas delivery apparatus 44 and the ESG 46 (FIG. 4) extends into the rear of the open interior of the handle 104. The coupler assembly 102 operatively connects the nozzle and electrode support assembly 100 to the end of the cord 48 within the handle 104. The handle 104 generally supports the elements within the pencil and is grasped when using the pencil 42.

The coupler assembly 102 includes a cord retainer 106 which connects to the forward or leading end of the cord 48. The retainer 106 includes a plurality of rearward facing tubes 108 having passageways 110 formed therethrough. Each of the tubes 108 is inserted within one of the lumens 50 and 74 of the cord 48. The passageways 110 conduct the gas in the lumens 50 and 74 through the retainer 106. A center opening 112 is formed in the retainer 106, and the electrical conductor 56 of the cord 48 extends through the center opening 112. An adhesive is applied to the exterior surface of the tubes 108 and within the interior of the center opening 112 to hold the cord 48 in place.

The supply conductor 56 of the cord 48 extends forward past the tubing retainer 106. An electrical connector 114 is electrically connected to the forward end of conductor 56. The electrical connector 114 is positioned in front of the forwardmost surface of the tubing retainer 106. As is shown in FIG. 6, the electrical connector 114 fits within and is retained by a receptacle 116 formed in a rear wall or partition portion 118 of a coupler sleeve 119 of the coupler assembly 102. A shoulder 120 at the forward end of the receptacle 116 prevents the electrical connector 114 from being pulled forward relative to the coupler sleeve 119 during use of the pencil.

The coupler sleeve 119 holds the electrical connector 114 and the tubing retainer 106 in position within the interior of the handle 104 as a result of inserting the coupler sleeve 119 into the forward open end of the handle 104. The handle 104, which is preferably made of silicone tubing, is expanded in a chemical substance to allow the coupler sleeve 119 to fit within the handle interior, and after removal from the chemical substance, the handle 104 returns to its original size. A shoulder 122 of the handle 104 contacts a correspondingly shaped annular ridge 124 of the coupler assembly to prevent withdrawal of the coupler sleeve 119.

Ports 126 are formed through the partition portion 118 at locations which correspond to and are in alignment with the passageways 110 in the retainer 106. The ports 126 thus continue the conduits for the gas in the lumens 50 and 74 forward through the partition portion 118.

A joining gasket member 128 is inserted through the forward open end of the coupler sleeve 119 and contacts the partition portion 118. The gasket member 128 includes a plurality of rearwarding facing tubing extensions 130 which fit within the ports 126 in the partition portion 118. Conduits 132 are formed through the gasket member 128 and tubing extensions 130 for the purpose of conducting the gas forward from the lumens 50 into the interior 134 of the nozzle and electrode support assembly 100. A center opening 136 is also formed in the gasket member 128 in alignment with the electrical connector 114. The rear end of the electrode 58 extends through the center opening 136 to electrically connect with the connector 114. The gasket member 128 is preferably formed from flexible silicone material, and a gas tight seal is established around the rear end of the electrode 58.

The nozzle and electrode support assembly 100 includes a forward portion 138 which extends forward beyond the forward end of the handle 104. The interior 134 of the forward portion 138 channels the gases flowing therethrough into a funnel-like configuration 140 and into the nozzle 52. The funnel-like configuration 140 and the length and diameter relationship of the nozzle 52 cause the gases to exit the nozzle 52 in a substantially directed or laminar stream or jet 54 (FIG. 4).

The gases within the nozzle 52 surround and flow along the centrally-positioned, forward, unsupported end of the needle electrode 58. A plurality of radially oriented ribs 142 extend axially along a rear end portion of the assembly 100, as is shown in FIGS. 6, 8 and 9. The ribs 142 support a center axially extending core 144 within which the needle electrode 58 extends and is rigidly retained. In addition to supporting the center core 144 and the needle electrode 58, the ribs 142 act to channel, direct and smooth the flow of gas to the nozzle 52. An alignment protrusion 146 extends outward from the forward end portion 138 and fits within a notch 147 formed in the coupler assembly 102, to properly orient the assembly 100 in the pencil, as shown in FIGS. 5 and 8.

A sector-shaped sensing plate 148 is connected to at least one of the ribs 142 and extends radially and perpendicularly outward from the needle electrode 58 and core 144 at the rear end of the assembly 100, as is shown in FIGS. 5, 6 and 9. At the outer marginal edge of the sensing plate 148, a pair of circular shaped protrusions 150 extend rearwardly from the sensing plate 148. A channel 152 extends between the center indention surrounded by the protrusions 150. When the assembly 100 is frictionally inserted and connected to the coupler assembly 102, as is shown in FIG. 6, the protrusions 150 align with two of the conduits 132a and 132b (FIG. 5) formed in the gasket member 128. The sensing plate 148 contacts the gasket member 128 in a fluid-tight manner and causes a fluid-tight passageway through the channel 152 between conduits 132a and 132b. The conduit 132a is in fluid communication with one gas supply lumen 50 and the conduit 132b is in fluid communication with the sensing lumen 74 (FIG. 5).

When the nozzle and electrode support assembly 100 is correctly retained in the pencil 42, a fluid tight passageway exists from one gas supply lumen 50 through the pencil and back through the sensing lumen 74. Gas pressure and flow is conducted back through the sensing lumen 74 to the gas delivery apparatus 44 (FIG. 4) where the pressure and flow are sensed to establish a proper connection of the nozzle and electrode support assembly 100. The ESG will deliver electrical energy only after the nozzle and electrode support assembly 100 has been properly inserted within the pencil.

A resilient gasket 154 extends circumferentially around an inner flange 156 of the assembly 100 for the purpose of providing a gas-tight seal between the assembly 100 and the coupler assembly 102, as shown in FIG. 6. The gasket member 128 makes a fluid tight seal around the rearward end of the needle electrode 58 when the assembly 100 is retained in the pencil, due to the resiliency of the material from which the gasket member 128 is formed. The compression of the resilient gasket member 128 and gasket 154 establish a fluid tight connection for confining the flow of gas from the lumen 50 in the cord 48 into assembly 100 and out of the nozzle 52.

The needle electrode 58 is preferably made of conductive metallic material. Preferably, the other portions of the nozzle and electrode support assembly 100 and the coupler assembly 102 are made of moldable polysulfone plastic or resilient material.

Access for cleaning is available as a result of making the nozzle and electrode support assembly 100 removeable from the pencil 42. Compared to constructing it as a single integral unit, the pencil 42 can be disassembled for cleaning or replacement of parts. Cost savings from the reuse and replacement of parts is an important feature of the pencil 42. If a new or different nozzle assembly is needed during the course of the surgery, it can be quickly replaced. The nozzle and electrode support assembly 100 can be made disposable, and the remainder of the pencil used repeatedly. The portion of the pencil excluding the nozzle and electrode support assembly can be manufactured in the manner described to withstand numerous sterilizations before it is necessary to replace it.

To accommodate the important aspects of a removable and/or disposable nozzle assembly 100 of the pencil, and to achieve safety in preventing operation of the ESU when the nozzle assembly 100 is not properly attached, the ESU of the present invention provides means for sensing the proper connection of the nozzle and needle support assembly 100 in the pencil. The cooperative arrangement provided by the sensing plate 148 and the separate gas delivery and sensing lumens 50 and 74, respectively, in the cord 48 achieve significant and desirable improvements with respect to safety in operation of an ESU of the type described.

Another significant improvement available from the pencil 42 is the reduction in stray leakage capacitance paths. Due to the operating frequency and voltage of the electrical energy supplied over the supply conductor 56 and electrode 58, there is some potential for radiation and leakage transmission to the hand of the surgeon and the surrounding environment, as is the case with virtually every type of ESU. By locating the electrical energy supply conductor within and surrounded by the gas containing lumens 50 and 74, the length of the capacity coupling path to the exterior environment of the cord is maximized. Reductions in leakage current through the stray capacitance occur by increasing the length of the stray capacitance path. Reduction of the leakage capacitance is extremely important, because the amount of electrical energy conducted through this path is reduced. Similar reductions in leakage capacitance along the length of the cord 48 also result because of the center location of the supply conductor 56 in the cord 48.

Gas Delivery Apparatus

The gas delivery apparatus 44 is shown in greater detail in FIG. 10. At least one source of gas 200, and preferably a second different source of gas 202 are provided. A different type of gas is employed in each of the macro and micro modes of operation of the ESU. Conduits 204 and 206 respectively conduct the gas from the sources 200 and 202 to a conventional gas select valve 208. An electrical signal-actuated valve drive 210 controls the mechanical elements within the valve 208. According to the predetermined signal applied to the valve drive 210, gas from the selected one of the sources 200 or 202 is conducted through the gas select valve 208 to a conventional pressure regulator 212. The pressure regulator 212 delivers the selected gas at a constant predetermined pressure to a conventional gas delivery valve 214. A valve drive 216 controls the gas delivery valve 214 to open and close, in accordance with an electrical signal applied to the valve drive 216. When the gas delivery valve 214 is actuated to an open condition by the valve drive 216, gas flows through the valve 214 to a filter 218. The filter 218 is of the typical "HEPA" type, which filters the gas flowing therethrough and removes any particulates and pathogenic organisms above a certain size, for example 0.3 microns.

Gas from the filter 218 is applied to a conventional flow controller 220. The flow controller 220 operatively controls the flow or quantity of gas passing therethrough to the a conduit 222. The gas flowing in the conduit 222 is conducted into the lumens 50 in the cord 48 (FIG. 4). The amount of gas flowing through the flow controller 220 is established in relation to an electrical signal applied thereto.

The gas delivery valve 214 selectively controls the delivery of gas to the pencil. As will be explained, the signals to the valve drive 216 for the gas delivery valve 214 are selectively originated by the surgeon. The quantity of gas flowing to the pencil, as established by the flow controller 220, is selected by the surgeon according to the type of surgical procedure and the type of gas (from one source 200 or 202) used during the procedure.

In order to determine proper gas delivery conditions before applying electrical energy to the pencil, the gas pressure and delivery conditions are sensed by two pressure transducers 224 and 226. The pressure transducers 224 and 226 are respectively connected in the gas flow path before and after the flow controller 220. Transducer 224 supplies a signal corresponding to the pressure of the gas delivered to the flow controller 220. The presence of gas pressure at the transducer 224 indicates that the selected one of the sources 200 or 202 is operative. Transducer 226 supplies signals relating to the pressure of the gas in the lumens 50 in the cord 48 and within the interior 134 of the nozzle 52 in the pencil 42 (FIGS. 5 and 6). The amount of gas pressure at the transducer 226 can indicate a variety of conditions. If the gas pressure is high, an obstructed cord or pencil may be indicated. An excessively low pressure may indicate a disconnected nozzle and electrode support assembly or a broken cord. Comparing the signals supplied by the transducers 224 and 226 is a technique for determining the proper gas delivery conditions for the ESU.

In order to further determine the proper attachment of the nozzle and electrode support assembly 100 within the pencil 42 (FIGS. 5 and 6), the pressure and the flow rate of the gas in the sensing lumen 74 are sensed. The gas pressure and flow rate from the sensing lumen 74 (FIG. 4) of the cord is applied to a conduit 228. A pressure transducer 230 provides signals indicative of the pressure. A conventional venturi tube 232 is connected to the conduit 228 and provides signals to a transducer 234 representative of the flow rate of the gas. By obtaining a signal representative of the pressure in the sensing lumen, from the pressure transducer 230, and by obtaining a signal representative of the flow rate of gas returned through the sensing lumen, through the venturi tube 232, it is possible to determine that the nozzle and electrode support assembly of the pencil has been properly attached and retained within the pencil. The signals from the pressure transducer 230 will be reduced when the nozzle and electrode support assembly 100 is not fully inserted within the coupler assembly (FIG. 6). Under such circumstances, the sensing plate 148 would be axially spaced from the gasket member 128, and the channel 152 between the conduits 132a and 132b (FIG. 7) would not establish a fluid tight passageway. Also under such circumstances, either the pressure or the flow rate would be diminished in the sensing lumen 74, which is communicated to the conduit 228 as shown in FIG. 10. Of course, a similar situation would exist if the nozzle and electrode support assembly was inserted within the interior of the pencil in an incorrect position, even though such attempts should be impossible due to the alignment protrusion 146 (FIG. 8).

Connectors for connecting the conduits 222 and 228 to the lumens of the cord 48 and for making an electrical connection from the ESG 46 to the conductor 56 of the cord 48 (FIG. 4) are illustrated in FIGS. 11A and 11B. A female connector 240, shown in FIG. 11A, is retained within a housing 241 of the ESG and the gas delivery apparatus. An insulated electrical conductor 242 delivers the electrical energy to the connector 240. The conductor 242 is electrically connected to center pin receptacle 243 located in the axial center of a female receptacle 244. Tubes 246 extend outward from the rear of the connector 240. A manifold disc 248 is positioned within the interior of the connector 240 for the purpose of communicating gas from the interior 250 of each tube 246 to an internal passageway 252 in a resilient sealing disc member 254. The tubes 246 and the passageways 252 are arranged in a circumferential pattern at the rear end of the connector 240 and within an interior receptacle 244, respectively. A female threaded portion 256 of a locking nut is also part of the connector 240.

The male connector 260, shown in FIG. 11B, includes a forward end portion 262. A plurality of passageways 264 are formed axially through the forward end portion 262. Each of the passageways 264 communicates with a conduit 266 formed in and extending through a center connector piece 268. Tubing portions 270 extend rearwardly of the connector piece 268 and define the conduits 266. The tubings 270 extend into the lumens 50 (and 74, not shown) of the cord 48. The supply conductor 56 of the cord 48 extends through a center hole 272 in the connector piece 268. A forward projection 274 of the center connector piece 268 supports the conductor 56 in the forward end portion 262. A male pin connector 276 is electrically connected to the outer end of the supply conductor 56. A rotatable nut 278 is connected to the connector 260 behind the forward end portion 262. To firmly retain the cord 48 within the connector 260 an adhesive is applied around the exterior of the tubing portions 270 before they are pressed into the lumens 50 and 74. Adhesive is also applied around the insulation of the supply conductor 56 to retain it firmly within the center hole 272 of the connector 268. The rotatable nut 278 is next attached and the forward end portion 262 is attached by an adhesive to the center connector piece 268.

To connect the connectors 240 and 260, the forward end portion 262 is inserted into the receptacle 244. The forward male pin connector 276 extends into the receptacle of the female pin connector 243. Each of the passageways 264 aligns with one of the passageways 252 due to an alignment rib 277 in the receptacle 244 fitting within a slot 279 of the forward end portion 262. The nut 278 is tightened within the internal receptacle, by threading the threads on the nut 278 into the threads of the female threaded portion 256. A fluid tight passageway therefore exists from the tube interior 250, through the passageways in the manifold disc 248, the passageways 252 and 264 and through the conduits 266 into the lumens 50 and 74 of the cord 48 (FIG. 5).

A separate hose is connected over each of the tubings 246. These hoses are connected to a common manifold to which the conduit 222 (FIG. 10) supplies gas. The one of the tubings 246 which is in communication with the sensing lumen 74 (FIG. 4) is connected by a separate hose to the conduit 228 (FIG. 10).

Use of the connectors 240 and 260 allows relatively convenient replacement of the cord 48 and attached portions of the pencil 42 (FIG. 6) when desired or necessary. The cord and the pencil portions can be sterilized as desired. The connectors 240 and 260 also serve as means for conducting electrical energy to the centrally located supply conductor 56 along the full extent of the cord 48, thereby securing the previously described advantages of reductions in leakage current and increased safety against the unintentional excessive transmission of electrical energy other than at the surgical site.

Electrosurgical Generator (ESG)

The major elements of the ESG 46 are illustrated in FIG. 12. The gas delivery apparatus 44 has previously been described in conjunction with FIG. 10. A control switch 300 supplies signals to initiate the delivery of the gas to the pencil and to initiate both the delivery of gas to the pencil and the application of electrical energy to the gas jet. The jet of gas from the pencil, not conducting electrical energy, can be applied by the surgeon to clear fluids from the tissue or to dry the tissue, usually prior to applying power to create an electrosurgical coagulation effect. Once the accumulated fluid has been driven away by the gas stream, the gas flow during coagulation sufficiently clears the fluids to achieve better coagulation effects.

The ESG 46 includes a front panel control 302. Various control devices, such as switches and potentiometers, provide signals to establish the selected amount of electrical power to be delivered during coagulation, the selected flow rate of the gasses delivered from the pencil, the one of the two gas sources 200 or 202 (FIG. 10) from which gas will be delivered, and other things. The signals for controlling the gas delivery apparatus 44 are routed through the front panel control 302 to the gas delivery apparatus 44. The gas flow and pressure signals from the pencil are also routed through the front panel control 302 to determine the proper connection of the nozzle and electrode support assembly 100 (FIGS. 5 and 6) of the pencil prior to delivering electrical energy.

A logic control circuit 304 is the main controlling component of the ESG 46. The logic control 304 interprets the signals from the control switch 300 to enable the delivery of gas and electrical energy to the pencil. Gas-related alarm conditions are detected by the logic control 304 in response to the gas-related alarm signals supplied by the gas delivery apparatus 44. The logic control 304 prevents the delivery of radio frequency electrical energy to the pencil until all energy requests and gas alarm conditions have been satisfied.

When the logic control 304 receives all of the proper enabling signals, a power supply control 306 is activated by signals from the logic control 304. The power supply control 306 controls a power supply 308. The power supply 308 receives electrical energy from conventional AC power source 310. The power supply control 306 controls the power supply 308 to deliver a predetermined amount of electrical power. Feedback signals are supplied from the power supply 308 to the power supply control 306 for the purpose of power control.

Electrical power at a predetermined level is delivered from the power supply 308 to an RF drive circuit 312. The logic control 304 delivers RF switching signals to the RF drive 312, thereby causing the RF drive 312 to selectively couple energy from the power supply 308 to a resonant output circuit 314 at a frequency established by the RF drive pulses. Energy is transferred from the resonant output circuit 314 to the pencil 42, and current is returned to the resonant output circuit 314 from the patient plate 70 (FIG. 4). The RF drive 312 charges the resonant output circuit 314 at a predetermined frequency established by the RF drive pulses, and the resonant output circuit 314 discharges at its resonant frequency by conducting electrical energy to the tissue at the surgical site.

An arc sense circuit 316 operatively switches the amount of electrical energy delivered between one of a plurality of levels during fulguration: specifically, a predetermined maximum target power level, a predetermined minimum target power level, and a predetermined active delivered power level. The arc sense circuit 316 provides signals to the logic control 304 which operatively control the amount of electrical energy conducted from the power supply 308 and RF output drive 312 to the output circuit 314. When the pencil is not within a predetermined operative distance from the tissue, the maximum target electrical power level is delivered from the pencil. The maximum target power level is automatically reduced to a minimum target electrical power level when the pencil is moved into predetermined sufficiently-close proximity to the tissue. The predetermined sufficiently-close proximity is determined as a result of signals from the resonant output circuit applied to the arc sense circuit 316. If the pencil remains in the predetermined close proximity to the tissue, the power level is automatically switched to the active power level. After the pencil is removed from the tissue, the power level automatically switches back to the maximum target level. The arc sense circuit 316 determines the proper power delivery levels by sensing arcing conditions as reflected by signals in the resonant output circuit 314.

To obtain desiccation, which is more gentle and less aggressive than fulguration, a considerably lower active electrical power level is continuously delivered to the pencil, and a different gas is preferably employed. When the pencil is substantially spaced away from the tissue, the continuously applied electrical power creates a coronal discharge in the gas jet issuing from the pencil. This coronal beam can be used to aim or direct the point at which the active level of electrical power will be applied to the tissue. As the pencil moves into sufficiently-close proximity with the tissue, the length of the coronal beam grows until full conduction occurs through the gas jet from the pencil to the tissue. The arc sense circuit 316 does not function during desiccation, because the active level of power applied for desiccation is relatively low and switching between different levels is unnecessary.

The control switch 300 is a conventional item, such as a conventional foot control switch used in electrosurgery, and is therefore not shown in detail. The control switch 300 might also take the form of a finger manipulated electrical switch positioned on the pencil. The two signals delivered by the control switch are a "CS gas" signal shown in FIG. 14 as applied at 320 and a "CS coag" signal applied at 322. The CS gas signal results when the surgeon desires to deliver only the gas jet from the pencil, without the application of electrical energy to the gas jet. The CS coag signal results when the surgeon desires to deliver both the selected flow of desired gas and electrical energy to the tissue.

The CS coag signal initially establishes the maximum target power delivery level in the gas jet during fulguration, and the selected active power delivery level for desiccation, depending on whether the macro or micro mode of operation has been selected respectively. Thereafter, the arc sense circuit causes the logic control 304 to automatically switch to the active predetermined power delivery level for fulguration upon movement of the pencil into predetermined proximity with the tissue.

The front panel control 302 is shown in greater detail in FIG. 13. A switch 324 is provided to select the type of gas delivered from one of the gas sources 200 or 202 (FIG. 10), depending upon whether fulguration or desiccation is desired. A "gas source" signal is applied at 326 according to the position of the switch 324. The presence of the gas source signal at 326 indicates a selection of one or the other of the gas sources, and the absence of the gas source signal at 326 indicates the selection of the other gas source.

A switch 328 is provided to select between the two different types or modes of coagulation effects, either fulguration or desiccation, available from the present invention. The fulguration coagulation effect is created when the electrical energy is transferred by arcs in ionized gas pathways to the tissue, and this type of operation is described as a "macro" mode of operation due to its substantially greater aggressive tissue effects. The desiccation coagulation effect is created by diffusely coupling relatively low amounts of electrical energy as a non-arcing current in a jet of preferably a different type of gas flowing at a relatively low flow rate, and this type of operation is described herein as a "micro" mode of operation. In the macro mode of operation, voltage from a source 330 is coupled through the switch 328 to an indicator bulb 332. The signal level at 334 is at a logical low level, indicating a macro level of operation is selected. Movement of the switch 328 to the other position applies the voltage from source 330 to create a logical high level at 334, thereby lighting an indicator bulb 336 and providing an indication of micro operating conditions. The signal at 334 is a "micro/macro" signal, and the low and high levels of this signal represent the macro and micros modes of operation, respectively.

If desirable, the switches 324 and 328 can be connected together, so that one specific gas source is always applied with a specific mode of operation, and vice versa.

A flow rate potentiometer 338 allows the surgeon to select the desired flow rate of gas issuing from the pencil in the jet. A signal from the potentiometer 338 is applied to a buffer 340. A "V Flow" signal is supplied at 342, and the V Flow signal is an analog signal related to the signal from the potentiometer 338. The V Flow signal 342 relates to the selected volume of gas to flow from the pencil.

Another potentiometer 344 allows the surgeon to select a predetermined level or amount of active power to be delivered from the pencil, in either the macro or micro modes of operation. A buffer 345 receives the signal from the potentiometer 344 and supplies a "V Act" signal at 348. The V Act signal 348 is an analog signal related to the maximum amount of voltage or active power which the surgeon has selected. The signal from the potentiometer 344 is also applied to a scaler 346 along with the micro/macro signal 334. When the micro/macro signal 334 is low, the scaler 346 changes the level of the signal created at the potentiometer 344 to a predetermined scale level. When the micro/macro signal 334 is high, the signal supplied by the scaler 346 is scaled to a different predetermined level. The signals from the scaler 346 are applied to an analog to digital converter, segment driver and multiplexer 350. The signal from the scaler 346 changes the display scale or gain created by the multiplexer 350.

The A to D converter, segment driver and multiplexer 350 receives a "VF Dig" signal at 356 and the analog signal from the scaler 346 which represents the active amount of power selected by the surgeon according to the selected mode of operation. As will be seen from the description of FIG. 10, the VF Dig signal 356 is a digital signal which represents the selected flow rate of the gas represented by the analog signal 342. Under control of multiplexing signals applied at 352, the multiplexer 350 converts the signal from the scaler 346 to a digital form and energizes a display 354 in accordance with flow rate and power level signals. The display 354 includes a portion which indicates the predetermined amount of active power selected for delivery during coagulation, and a portion which indicates the selected maximum gas flow rate.

As is shown in FIG. 10, the logic control of the ESG 46 includes a flow alarm logic circuit 360 which receives the pressure signals from the transducers 224, 226, 230 and 234. The flow alarm logic 360 includes conventional digital logic elements for determining the appropriate flow conditions from the signals supplied by the transducers. The flow alarm logic circuit 360 is enabled to respond and supply the described signals by application of a gas source signal at 360. The gas source signal at 326 also controls the flow logic alarm 360 to establish different alarm levels relative to the source of gas selected. Should a low flow or reduced amount of gas be delivered by the gas delivery apparatus 44, a signal will be supplied at 361 to an oscillator 364. The oscillator 364 switches the signal at 361 at a relatively low switching rate and supplies a "low flow" oscillating signal at 362. The low flow signal at 362 will energize a transistor 366 and indicator lamp 368, as shown in FIG. 13. An audible alarm 370 will also be energized under low flow conditions by the flow alarm logic 360 as shown in FIG. 10. Thus, under low flow conditions, a flashing lamp 368 (FIG. 13) and an alarm at 370 will all be energized to alert the user of low gas flow conditions. Alarm level conditions are determined primarily by sensing and comparing excessively high or low pressures represented by the signals at 224, 226 and 230.

Under conditions where a flow fault exists at the pencil, which will be determined by the presence or absence of pressure and gas flow in the sensing lumen 74 (FIG. 4) and conduit 228, as shown in FIG. 10, the flow alarm logic 360 will supply a flow fault signal at 372. The flow fault signal at 372 energizes a transistor 374 and an RF disconnect indicator lamp 376, as shown in FIG. 13. A "flow alarm" signal is created at 378. The flow alarm signal at 378 is operative for inhibiting the generation of electrical energy from the ESG under flow fault conditions.

A "gas valve" signal at 380 is ultimately established when the control switch 300 (FIG. 12) supplies either one of the CS gas or CS coag signals at 320 or 322, respectively, to the logic control circuit 304 (FIG. 14). The gas valve signal exists at 380 so long as the control switch is manipulated to request the delivery of gas from the pencil, and for a predetermined delay period after release of the switch, e.g. for five seconds. This delay period allows the surgeon to switch the electrical power on and off quickly during the procedure without also terminating the gas flow. The gas valve signal at 380 controls the valve drive 216 to open the gas delivery valve 214 of the gas delivery apparatus 44, as shown in FIG. 10, to deliver gas to the pencil.

The gas source signal at 326 from the switch 324 (FIG. 13) is applied to a gas selection and scaler logic element 382, as shown in FIG. 10. The gas selection and scaler logic element 382 supplies an operating signal to the valve drive 210, in accordance with the level of the gas source signal at 326. The valve drive 210 operates the gas select valve 208 to select the one of the two gas sources 200 or 202 from which to deliver gas to the pencil. The element 382 also converts the analog V Flow signal at 342 to digital form, scales it, and supplies it at 356 as the VF Dig signal. The scaling level for the VF Dig signal is established by the gas source signal at 326, according to the source of gas selected.

The signal which controls the flow controller 220 is delivered from a dial to flow voltage converter 384. The V Flow signal at 342 is applied to the converter 384 and serves as the primary signal for establishing the gas flow rate through the flow controller 220. The gas valve signal at 380 is also applied to the converter 384, for the purpose of controlling the application of the control signals to the flow controller 220 in smooth transition with the activation of the gas delivery valve 214 to avoid pressure and flow overshoots or surges. The gas source signal is also applied to the converter 384 for the purpose of controlling the flow controller 220 in a linear manner relative to the selected type of gas.

Details of the logic control 304 are shown in FIG. 14. The CS gas signal at 320 and the CS coag signal at 322 are individually supplied from the control switch 300 (FIG. 12) to a control logic element 386. The logic element 386 supplies a signal at 388 when only the delivery of gas from the pencil is required. The signal at 388 is applied to a delay element 390. The delay element 390 immediately applies a signal at 392 upon the application of the signal at 388. However, the delay element 390 delays the removal of the signal at 392 for a predetermined time period after the signal at 388 has terminated. The signal at 392 is applied through an OR gate 394, and the output signal from the OR gate 394 becomes the gas valve signal at 380. The gas valve signal at 380 operatively controls the delivery of gas to the pencil, among other things, as has been described. The delay element 390 prevents the immediate termination of the gas flow through the pencil to allow the surgeon to rapidly switch the electrical power on and off during the procedure without terminating the gas flow.

Upon the control logic element 386 receiving a CS coag signal at 322, a signal is applied at 396. The signal at 396 becomes a "REQ" signal, indicating a request for the delivery of electrical power. The signal at 396 is also applied to the OR gate 394. Thus, either a signal at 396 or a signal at 394 creates the gas valve signal at 380. Accordingly, the request for either gas from the control switch (a CS gas signal at 320), or the request for an electrosurgical coagulation signal (the CS coag signal at 322), will result in the creation of a gas valve signal at 380. A time delay 398 receives the signal at 396. The delay 398 applies a "KHV" signal at 400 at a predetermined time period after the REQ signal at 396 has gone low.

The REQ signal at 396 is applied to the power supply control 306 (FIGS. 12 and 16) for the general purpose of initiating the delivery of power from the power supply 308 (FIG. 10). The KHV signal at 400 is ultimately applied to the power supply 308 for the purpose of "killing" or terminating the supply of high voltage delivered from the power supply to the RF output drive 312 (FIG. 12).

Referring to FIG. 14, the logic control 304 also includes a frequency generation clock 402. The clock 402 includes the conventional frequency source, such as a crystal oscillator. The clock 402 also includes conventional frequency dividing elements for supplying the signals at 352. The signals at 352 are, of course, applied to the converter, driver and multiplexer 350 (FIG. 13). The clock 402 also supplies a 1 MHZ clock signal at 406. The signal at 406 is the highest frequency supplied by the clock 402, and this frequency is used for deriving other lesser frequency signals for controlling the output RF energy applied to the pencil, for synchronizing switching in the logic elements of the ESG, among other things.

A frequency divider 408 receives the clock signal at 406. The divider 408 supplies four predetermined lesser frequency signals at 410, 412, 414 and 416. The frequency signals at 410, 412, 414 and 416 are used primarily throughout the ESG to control the application and duration of the energizing or drive pulses delivered to the resonant output circuit 314 (FIG. 12). The frequency signals 410, 412, 414 and 416 are applied to a drive pulse generator 418 which operatively creates "drive pulses" at 420. The drive pulses at 420 are applied to the RF drive circuit 312 (FIGS. 12 and 17) for the purpose of controlling the application of energy from the power supply 308 to the resonant output circuit 314 (FIG. 12).

A "target/active" signal is applied at 422 from the arc sense circuit 316 (FIGS. 12 and 19), when operating in the fulguration mode. The level of the target/active signal at 422 operatively controls the level of electrical energy delivered during requests for fulguration coagulation effects. An AND gate 424 receives the target/active signal at 422 and the signal at 396 at its input terminals. Upon the presence of both high signals at 422 and 396, the AND gate 424 supplies a "TAR" signal at 426. The TAR signal at 426 is present during the delivery of a target level of electrical energy to the needle electrode of the pencil. The use of a target level of energy also reduces the amount of radio frequency energy which leaks or is transmitted to the surrounding environment during times when electrosurgical effects are not desired or possible, usually when the pencil is spaced too far from the tissue.

The target/active signal 422 is inverted by invertor 428 and the inverted signal is applied to one input of an AND gate 432. The other input to the AND gate 432 is the signal at 396. When the target/active signal at 422 is low and the REQ signal at 396 is high, an "ACT" output signal from the AND gate 432 is applied at 434. The ACT signal is present when the ESG supplies the active or predetermined maximum amount of power selected by the surgeon at the front panel control 302 (FIGS. 12 and 13).

When the target/active signal 422 is high, a target level of power is supplied, and the TAR signal is delivered. When the target/active signal 422 is low, an active or maximum level of power is supplied, and the ACT signal is delivered. The inverted target/active signal at 430 is also applied to the drive pulse generator 418 and is used to control the delivery of the drive pulses 420.

The ACT signal at 434 is applied to the transistor 436 of the front panel control 302, as is shown in FIG. 13. The ACT signal energizes the transistor 436, thereby causing the indicator bulb 438 to light, indicating that the active amount of electrical power is being delivered to the pencil.

Referring back to FIG. 14, an "ACK" signal 440 is applied to the logic control 304 from the power supply control 306 (FIG. 16). As will be described more completely in conjunction with the description of the power supply control 306, the ACK signal at 440 occurs after the application of the REQ signal at 396 and after the power supply approaches to a predetermined extent the desired active energy delivery level. The ACK signal thereby serves as an acknowledgement that the power supply is operating.

The ACK signal at 440 and the flow alarm signal at 378 are applied to a delay logic circuit 442. The delay logic circuit 442 delivers a "CGEN" signal at 444 a predetermined time after the application of both the ACK signal at 440 and the flow alarm signal at 378. The delay logic element 442 logically establishes that the power supply is properly operating (receipt of the ACK signal 440) and that there are no gas flow alarm conditions which would inhibit proper operation of the ESG (termination of the high level of the flow alarm signal 378) before delivering the CGEN signal. With reference to FIG. 13, it can be seen that the proper operation signal level for the flow alarm signal at 378 is a high level signal, which occurs when a flow fault signal at 372 is not energizing transistor 374. The CGEN signal at 444 is delivered at a predetermined time after the establishment of the proper conditions dictated by the signals at 378 and 440.

The drive pulse generator 418 supplies the drive pulses at 420 in response to the presence of the CGEN signal at 444 and the target/active signal at 422, as shown in FIG. 14. The target/active signal at 422 and the CGEN signal at 444 are applied to the input terminals of an AND gate 446. The output signal from the AND gate 446 is applied to the clocking terminal of a flip flop 448. The application of a high signal to the clock terminal of the flip flop 448 causes a high output signal at the Q output terminal of the flip flop 448. The high signal from the Q output terminal and the target/active signal at 422 are applied to an AND gate 450. The output signal from the AND gate 450 is a booster control signal at 452.

The booster control signal at 452 is applied to the J terminal of a JK flip flop 454. The frequency signal at 416 is applied as a clocking signal to the clock terminal of the flip flop 454. With the next clocking pulse after the application of the booster control signal of 452, a high output booster signal at 456 is supplied from the Q output terminal of the flip flop 454. The booster signal at 456 is applied to one input of an OR gate 458. So long as one of the input signals to the OR gate 458 is present, a drive pulse signal will be present at 420. The duration of the booster signal at 456 is established by a one-shot multivibrator 460 which receives its input signal from the not Q terminal of the flip flop 454. A predetermined time after the not Q input signal goes low, the multivibrator 460 delivers a reset signal at 462 to reset the flip flop 454. The one-shot 460 therefore serves as means for limiting the maximum duration of each individual booster signal applied at 456 and the resulting booster drive pulse at 420. Each pulse of the booster signal at 456 is repeated in a pulse-like fashion so long as the signal at 452 remains high and pulses are applied at 416. Each pulse-like booster signal at 456 is initiated by each pulse of the frequency signal at 416 and is terminated by the reset signal 462 from the one-shot 460.

To limit the maximum time for application of the pulse-like booster signals at 456 and hence the booster drive pulses at 420, a one-shot multivibrator 464 is connected to the not Q output terminal of flip flop 448. After a predetermined maximum time duration during which it is desired to deliver the booster signal pulses as drive pulses, the multivibrator 464 delivers a reset signal at 466 to reset the flip flop 448. The signal at the Q output terminal of flip flop 448 goes low, thus terminating the booster control signal at 452, the booster signal at 456 and the booster drive pulses at 420. The booster drive pulses result after the active power level has been terminated and the target power level resumes, or upon the initial application of electrical power to the gas jet.

The purpose of the booster drive pulses is to initiate ionization of the gas jet of the pencil. Initiation of ionization in a reliable manner usually requires a different amount of energy than that for maintaining the ionized state in the gas. As is presently appreciated, the booster drive pulses at 420 are preferably wider in time duration than the target and active drive pulses. The wider time width duration of the booster drive pulses results in greater application of electrical energy to the electrode of the pencil. In general the wider booster drive pulses create a higher voltage on the electrode of the pencil. The higher voltages create a greater electric field, and the electric field surrounding the electrode initiates the ionized pathways within the gas jet.

The difficulty of initiating an ionized pathway between the electrode and the tissue is common to almost all types of electrosurgical apparatus, and is not necessarily limited only to those which conduct the electrical energy through in ionized gas jet. Accordingly, the concept of applying the booster pulses of slightly increased energy or width to initiate the ionized pathways is an improvement which finds applicablity in a variety of electrosurgical equipment.

The target drive pulses created at 420 are of a time width duration less than the booster pulses but are sufficient to maintain the ionized pathways and the targeting beam within the gas jet. To create the target drive pulses, the output signal from the Q terminal of the flip flop 448 is inverted by an invertor 468 and is applied to one input terminal of an AND gate 470. The target/active signal at 422 is applied to the other input terminal of the AND gate 470. After the signal at the Q output terminal of the flip flop 448 goes low, a high output signal will be supplied from the invertor 468. During target conditions, the level of the target/active signal at 422 is high. The AND gate 470 will then supply a high target control signal at 472 to the J input terminal of a clocked JK flip flop 474. Upon receipt of the first pulse of the frequency signal at 416, the JK flip flop 474 will initiate a pulse target signal at 476 from its Q output terminal. A one shot multivibrator 478 responds to the low level signal from the not Q output terminal of the flip flop 474 and supplies a reset signal at 480 to the reset terminal of the flip flop 474 upon the expiration of a predetermined time after the signal at 476 goes high. The flip flop 474 is reset and the signal at 476 goes low, thus creating an individual target pulse signal. The multivibrator 478 establishes the width of each target pulse. Target pulse signals are thus created so long as target control signal at 472 and the frequency signal at 416 are present. The target pulse signals at 476 are coupled through the OR gate 458 and become target drive pulses at 420.

The time duration of each individual pulse of the target pulse signal at 476 can be reduced by the application of a target power switch signal or "TPSW" signal at 482. The TPSW signal changes the time delay of the multivibrator 478 and reduces the width of the target pulse 476. The TPSW signal 482 is supplied by the arc sense circuit 316 (FIGS. 12 and 19) to prevent the ESG from rapidly switching or fluttering back and forth between the target and active levels of power, which could occur when the pencil is at distances where breakover between target and active power occurs. The TPSW 482 signal occurs when the arc sense circuit first senses an arc travelling from the pencil electrode to the tissue. The width of the target pulses is immediately reduced until a predetermined number of other arcs are sensed, which signifies that the pencil remains in sufficiently close proximity to apply full power. If a predetermined time has expired and another arc has not been sensed, the TPSW signal is terminated, causing the re-application of full-width target pulses. When the TPSW signal is present, the reduction in width and hence energy of the target pulses is not so excessive as to extinguish the ionized pathways in the gas jet.

The drive pulse generator 418 supplies active drive pulses at 420 upon the occurence of an active control signal at 430. The active control signal at 430 results when the target/active signal at 422 goes low, indicating a condition for the delivery of active coagulation energy. The active control signal at 430 is applied to the J input terminal of a clocked, edge-triggered JK flip flop 484. Upon the next transition of the frequency signal at 416, supplied to the clock terminal of the flip flop 484, an output pulse signal is initiated from the Q output terminal of the flip flop 484. Immediately thereafter, at a transition of a considerably higher frequency signal at 410, the flip flop 484 is reset. The output pulses from the flip flop 484 are applied to a pulse stretch circuit 486. Each of the pulses is reliably extended in time duration by a predetermined amount established by the pulse termination delay or stretch features of the circuit 486. An active pulse signal at 488 results and is supplied to the OR gate 458. The active pulse signal at 488 becomes the active drive pulses at 420 when no other signals are applied to the input terminals of the OR gate 458.

From the foregoing description, it can be understood that a high level of the target/active signal at 422 operatively controls the delivery of the booster pulse signals at 456 and target pulse signals at 476, and a low level target/active signal at 422 causes the delivery of the active pulse signal at 488. When the target/active signal at 422 is at a high level, the flip flops 448, 454 and 474 are activated in the manner described. When active coagulation power is desired, the target/active signal at 422 goes low, thereby disabling the flip flops 448, 454 and 474, but enabling the flip flop 484 which supplies the active pulse signals at 488. The inverter 468 assures that only one of the flip flops 454 or 474 will supply pulse signals at a time. The length of time which booster pulses are supplied is established by the time period of the one-shot multivibrator 464, and this time period is predetermined to obtain sufficient initial ionization in the gas jet to sustain the target pulses. After ionization is established and the multivibrator 464 times out, the flip flop 474 commences delivering the target pulse signal at 476 to maintain the ionization and create the corona discharge in the gas jet. The target pulse signal at 476 is present at either its full or reduced width until switching to active coagulation power level occurs, at which time the active pulse signal at 488 appears and the target pulse signal at 476 terminates. If the active pulse signal terminates as a result of the surgeon moving the pencil out of proximity from the tissue, the target pulse signal at 476 resumes. The booster pulse signal results only upon the occurence of each ACK signal at 440 and the change from an active power delivery level to a target power delivery level. The application of booster pulses insures that target pulses will be established at all times when active power is not present. Thus, only one type of pulse signal is applied at 456, 476 or 488 at a time to the input terminals of the OR gate 458. Proper operation of the drive pulse generator 418 is assured without overlap or confusion of the separate pulse signals at 456, 476 and 488.

Details of the power supply 308 are illustrated in FIG. 15. A conventional AC power source 310, such as a conventional 110 or 220 volt AC source, supplies electrical energy to the power supply 308 through a conventional connector 490. A primary winding 492 of a line transformer 494 receives the conventional AC power applied through a breaker 496. A secondary winding 498 of the line transformer 494 steps up or increases the output voltage to a predetermined maximum amount desired to be utilized by the electrosurgical generator. A high voltage triac 500 is connected in the circuit of the secondary output winding 498 of the line transformer 494. The high voltage triac 500 is fired or triggered by a "HVTR" signal applied at 502 during each half cycle of the alternating signal supplied by the secondary winding 494. By controlling the conduction time of the high voltage triac 500 during each half cycle, the amount of power delivered by the triac is controlled. The AC electrical power is supplied to a conventional diode rectifying bridge 504. The bridge 504 establishes a high voltage DC supply across a filter capacitor 506. This high DC voltage is applied to a high voltage smoothing filter 508 and to a resistor 510. A positive high voltage, "+HV" is present at 512, and a negative high voltage signal, "−HV" is present at 514. The high voltage DC electrical power is supplied from the power supply 308 at 512 and 514.

A "VSEN" signal at 516 relates or corresponds to the magnitude of the high voltage across the capacitor 506. A signal representative of the current conducted is supplied at 518, and is designated "ISEN". The ISEN signal at 518 is developed by current conducted through resistor 510. The VSEN signal at 516 and the ISEN signal at 518 are applied to the power supply control 306 (FIGS. 12 and 16) as feedback control signals for establishing the timing of the HVTR signal 502. In this manner the output power from the power supply 308 is regulated and controlled.

In the event that a request for active coagulation power is quickly terminated, the HVTR signal is terminated and the triac 500 becomes nonconductive. Shortly thereafter a resistor 520 is selectively connected across the capacitor 506 by a controllable switch 522. The KHV signal at 400 serves as the control signal for closing the controllable switch 522. When the controllable switch 522 closes, the resistor 520 quickly discharges the filter capacitor 506.

A relatively low voltage positive and negative DC power supply, with respect to a ground reference at 524, is provided by the rectifying bridge 526 and the positive and negative filter capacitors 528 and 530, respectively. A minor portion of the secondary winding 498 supplies the appropriate level of voltage to the rectifying bridge 526. The positive DC power is supplied at 532 and the negative DC power is supplied at 534. The power levels at 532 and 534 energize the logic and other control elements of the ESG. An "AC" signal is derived at 536 from the secondary winding 498. The AC signal at 536 serves as the signal for determining the zero crossing point of the AC power signal at the secondary winding 498, and is used for synchronizing the firing of the triac 500.

Details of the power supply control 306 are shown in FIG. 16. The VSEN signal at 518 and the ISEN signal at 516, which respectively correspond to the sensed voltage and current delivered from the power supply 308 (FIG. 15), are applied to buffer amplifiers 538 and 540, respectively. The output signals from the amplifiers 538 and 540 are a power supply voltage signal at 542 and a power supply current signal at 544, respectively. The power supply voltage and current signals are applied to the input terminals of a multiplier 546. The multiplier 546 multiplies the two input signals and supplies an output signal at 548 which relates to the power output of the power supply.

The power supply power output signal at 548 is applied to one input terminal of a power limiting circuit 550. Similarly, the power supply voltage signal at 542 is applied to one input terminal of a voltage limit circuit 552. The other input signals to each of the limit circuits 550 and 552 are derived from a scaling circuit 556, which includes a plurality of scaling resistors and transistor switches. Signals for controlling the opening and closing of the transistor switches of the scaling circuit 556 are a "MAC" signal applied at 558, a "MIC" signal applied at 560, and the TAR signal applied at 426. The MAC and MIC signals are derived from the macro/micro signal 334 (FIG. 13). An inverter 561 inverts the signal at 334 to create the MAC signal. Input signals which are scaled by the scaling resistors of the scaling circuit 556 are a predetermined voltage established by source 562, and the VACT signal applied at 348.

The presence of the MAC signal at 558 causes the VACT signal at 348 to be scaled and applied as the second input signals to the voltage limit circuit 552 and to the power limit circuit 550. A similar situation occurs with respect to the application of the MIC signal at 560, except that the magnitude of the signals applied at the power and voltage limit circuits 550 and 552 are respectively different, compared to the magnitudes of those signals applied when the MAC signal is present at 558. When the TAR signal is present at 426, the magnitude of the voltage source 562 is scaled down and applied to the second input terminals of the power and voltage limit circuits. In all cases, the scaling occurs as a result of the resistors which are connected in series with the input signal, as a result of the transistor switches becoming conductive. The values of the resistances have been chosen to provide predetermined appropriate values to the limit circuits against which the power supply voltage signal at 542 and power supply power output signal at 548 are compared. The signals at 564 and 566 become power and voltage limit signals.

The power limit circuit 550 compares the power supply power output signal at 548 with the power reference signal at 564, and supplies a power error signal at 572 which is related to the magnitude of the difference in the amount of power which the power supply 308 is actually supplying as compared to requested amount of power established by the VACT signal. Similarly, the voltage limit circuit 552 compares the power supply voltage signal at 542 to the voltage limit signal at 566, and supplies a voltage error signal at 573 which is related to the magnitude of the difference in the power supply output voltage relative to the maximum allowable output voltage established by the limit signal at 566.

The error signals 572 and 57 from the limit circuits 550 and 552, respectively, are of opposite polarity. For example, the power error signal at 572 from the power limit circuit 550 may be a positive-going signal, while the voltage error signal at 573 from the voltage limit circuit 552 is a negative-going error signal. The opposite polarity error signals 572 and 573 are applied to the input terminals of a conventional ramp generator 574. The opposite polarity error signals are added together in the ramp generator 574 to provide an overall error signal whose absolute magnitude is related to the difference in error signals at 572 and 573. This absolute magnitude error signal controls the ramp generator 574. An output signal at 576 from the ramp generator generally increases periodically with respect to time, with the rate of increase being related to the absolute magnitude of the error signal. The signal at 576 determines the phase angle firing point at which the triac 500 (FIG. 15) is triggered during every half cycle of the rectified AC power applied. A zero crossing signal is applied at 578 from a conventional zero crossing detector 580. The AC signal at 536 is applied to the zero crossing detector 580 for the purpose of establishing the zero crossing point signal at 578 in synchronization with the occurrance of each half cycle of rectified AC power in the power supply.

A phase angle pulse generator 582 supplies an output control pulse at 583 during each half cycle of the rectified AC line power, and the width and/or duration of this pulse is controlled by the firing point signal 576 and the zero crossing signal at 578. The half cycle control pulse signal 583 is applied to a logic circuit 584. The logic circuit 584 is triggered by the control pulse signal 583 and operatively controls a transistor 585 in relation to the control pulse signal 583. The transistor 585 is switched on and delivers the HVTR signal at 502 to control the triac 500 of the power supply 308 (FIG. 15).

The ACK signal at 436 is derived by an over-voltage gate circuit 586. The over-voltage gate circuit 586 receives the REQ signal at 396 and a signal from the voltage limit circuit 552. So long as the power supply voltage signal at 542 is less than or equal to the voltage request signal at 566, a gate control signal is present at 587. The over-voltage circuit 586 conducts the REQ signal at 396 as the ACK signal at 436 so long as the gate control signal is present at 587. The presence of the ACK signal at 436 thereby signifies that acceptable operation of the ESG is possible. The ACK signal 436 must be supplied to the logic circuit 584 to cause the control pulse signal 583 from the phase angle pulse generator 582 to be shaped and applied to the transistor 585.

Details of the RF drive 312 are illustrated in FIG. 17. Details of the resonant output circuit 314 are illustrated in FIG. 18. The RF drive 312 and the resonant output circuit 314 are essentially the same as those circuits which have previously been described in U.S. Pat. No. 4,429,694. Accordingly, the description herein will be simplified.

With respect to the RF drive circuit 312 shown in FIG. 17, the drive pulses at 420 and the master frequency 1 MHz signal at 406 are applied to a phase and timing control circuit 600. The phase and timing control circuit 600 delivers a series of phase driving pulses at conductor terminals 602 and 604. The phase driving pulses occur at a frequency established by the drive pulses at 420, as synchronized by the master frequency signal at 406. After delivering each phase driving pulse at 602 and 604, the phase and timing control circuit 600 delivers an extinguishing driving pulse at the terminals 603 and 605. The phase driving signals occur simultaneously at 602 and 604 and the extinguishing driving signals occur simultaneously at 603 and 605.

The signals at 602 and 603, and at 604 and 605 are respectively applied to their own switch drive circuit 608. For convenience of illustration, only one switch drive circuit 608 is shown in FIG. 17 connected to the terminals 604 and 605. Another switch drive circuit identical to that shown at 608, but not shown, is connected to the terminals 602 and 603.

Each switch drive circuit 608 includes its own center-tapped primary winding 610 of a single drive transformer 612. The driving pulse signal at 604 energizes the transistor 614 of the switch drive circuit 608, thereby causing the primary winding 610 of the drive transformer 612 to induce a magnetic flux in each of two output windings 618 of the drive transformer 612. The extinguishing pulse signal at 605 energizes the transistor 616 to induce an opposite magnetic flux in each of the output windings 618. Creating both positive and negative fluxes in the drive transformer 612 has the advantage of creating very quick and positive turn on and turn off conditions for the high current switches 620. This is a benefit because of the speed with which switching occurs in the resonant output circuit 314.

Two identical high current switches 620, each of which includes its own winding 618, is operatively connected to each drive transformer 612. Each high current switch 620 includes a pair of high current FET transistors 622 connected in parallel. Magnetic flux in the winding 618 creates a signal to energize the transistors 622 to conduct current between the switch terminals 624. An induced magnetic flux in the opposite direction in the windings creates a signal to turn the transistors 622 off. The transistors 622 in the other high current switches 620 are turned on and off simultaneously by the driving pulse and extinguishing pulses at 602 and 603. Accordingly all four high current switches 620 are rendered conductive and are rendered nonconductive simultaneously.

Details of the resonant output circuit 314 are shown in FIG. 18. Four high current switches 620 (see FIG. 17) are electrically connected in series. The application of the driving pulse signals causes all four high current switches 620 to become simultaneously conductive. The high voltage at terminals 512 and 514 from the power supply 308 (FIG. 15) charges a resonant circuit 632 during the time the high current switches 620 are conductive. A capacitor 630 is part of the resonant circuit 632 which also includes an output transformer 634, having a primary winding 636 and a secondary winding 638. The primary winding 636 is thus charged with high current electrical energy from conductors 512 and 514 when the high current switches 620 are simultaneously conductive. When the high current switches 620 are extinguished or nonconductive, the resonant circuit 632 commences oscillating at its natural frequency. The natural frequency is primarily established by the effective inductance of the primary winding 636 and the capacitance of the capacitor 630. An unloaded natural frequency of approximately 500-600 KHz has proved satisfactory. A sensing transformer 640 is connected in series in the resonant circuit 632.

Electrical energy is transferred from the resonant circuit 632 to the secondary winding 638 of the output transformer 634 and through isolating capacitors 642 to the pencil 42 and tissue 62 (FIG. 4). The impedance created within the pencil, the impedance experienced by the arcs in the ionized pathways of the gas jet, and the impedance or resistance of the tissue causes a damping effect on the electrical energy in the resonant circuit 632. To replenish the energy in the resonant circuit 632 after each ring down cycle, the high current switches 620 are switched on and off at a predetermined repetition rate, which is considerably less than the natural frequency of the resonant circuit 632 and the high frequency signal applied to the gas jet. Under loaded conditions, some inherent reactances in the tissue and energy delivery paths may actually modify the unloaded frequency of the high frequency surgical signal compared to the natural frequency of the resonant circuit.

The high frequency surgical signal is substantially non-radiating during the surgical procedure because the conductive pathways in the gas jet exhibit a lower resistance to energy flow than radiative energy pathways. As soon as the conductive pathways are established to the tissue, any radiating component of the energy transfer terminates due to the conductive aspects of the ionized pathways in the gas jet.

The sense transformer 640 of the resonant output circuit 632 supplies "+SNS" and "−SNS" signals at 644 and 646 respectively. These signals at 644 and 646 represent an indication of a loaded or an unloaded condition of the output transformer 634, and are employed by the arc sense circuit to change from target level of power delivered to an active level of power delivered.

Details of the arc sense circuit 316 are illustrated in FIG. 19. The +SNS and the −SNS signals from the resonant output circuit 318 (FIG. 18) are applied at 644 and 646 respectively. The various frequency signals are applied at 412, 414 and 416. The macro/micro signal is applied at 334, and the VACT signal is applied at 348, after having been conducted through the logic control 304 (FIG. 14) from the front panel control 308 (FIG. 13). The CGEN signal is applied at 444 from the logic control 304 (FIG. 14). From the application of these various frequency signals, the arc sense circuit 316 supplies the target/active signal at 422 to control the target or active level of electrical power delivered by the ESG to the pencil during the macro mode of operation. During the micro mode of operation, there is no switching of levels of electrical power delivered by the ESG due to the relatively low power delivered during the micro mode of operation. The TPSW signal is also delivered at 482 by the arc sense circuit 316. The TPSW signal is used to reduce the magnitude of the target power to a predetermined amount, to assure that the pencil has been moved into sufficiently close proximity with the tissue before switching to the active level of power, thereby preventing flutter between the active and target levels when the pencil is spaced at indeterminate positions where switchover would normally occur, as had previously been described.

The +SNS signal at 644 and the −SNS signal at 646 are applied across a Zener diode 648. The Zener diode prevents the signal level from exceeding a predetermined breakover level of the diode, and maintains the polarity of the signal applied to a gate or time window generator 650. The frequency signals at 412, 414 and 416 control the window generator 650 to create a short predetermined time period or time "window" during which the input signal applied to the generator 650 is conducted therethrough as an output signal applied at 654. This time window occurs during each ring down cycle of the resonant circuit 632 (FIG. 18). The frequency signal at 416 assures that the time window from the generator 650 occurs in synchronization with the the ring down cycle, because the frequency signal at 416 controls the energization of the high current switches 620 (FIG. 18) during which the resonant circuit is energized.

The signal across the Zener diode 648 represents the loading characteristics on the secondary winding 632 of the output transformer 634 (FIG. 18). Under load, the signal conducted during the time window established by the generator 650 will essentially be a constant level or a flat line, because the oscillations from the resonant circuit have been damped significantly by the load to which energy is coupled from the pencil. When the secondary winding 638 of the output transformer 634 (FIG. 18) is not under load, and no substantial current is being conducted, pulses will occur as the signals at 644 and 646, because no significant damping of the resonant circuit has occurred. During the time period when the time window is open, the generator 650 will conduct some of these pulses as a signal at 654, and these pulses will be applied as the input signal to the input terminal of the A to D converter 656.

The A to D converter 656 operates in synchronization with the frequency signal at 416. Thus, the converter 656 is triggered into operation once each ring down cycle in a predetermined synchronized relationship with the occurrence of each time window created by the window generator 650. The constant or flat-level signal at 654 appearing during the loaded conditions is converted by the converter 656 as a logical zero output signal applied at 658. The converter 656 supplies a synchronized pulse train at the frequency 416 when a pulsed signal at 654 represents an unloaded secondary winding of the output transformer of the output resonant circuit.

The signals at 658, either a logical zero or a synchronized pulse train, are applied to input terminals of a pulse burst detector 660 and a missing pulse detector 662. In general, the function of the missing pulse detector 662 is to examine the synchronized pulse train at 658 and determine when pulses from the pulse train are missing. After a predetermined number of sequential missing pulses has been determined, which represents the occurrence of a loading condition on the resonant output circuit, the missing pulse detector 662 supplies a signal indicative of the occurrence of a loading condition. The output signals from the missing pulse detector 662 are operatively used to switch the power output from the target level to the active level and/or to reduce the target level power to the predetermined amount to prevent flutter by supplying the TPSW signal. In general, the function of the pulse burst detector 660 is to examine the logical zero signal at 658 and to determine the occurrence of the synchronized pulses. Upon the occurrence of a predetermined number of synchronized pulses, the pulse burst detector 660 supplies the signal indicative that an unloaded condition has occurred. The output signal from the pulse burst detector 660 is operatively employed to cause switching of the electrical output power level from the active level to the target level.

Since the pulse burst detectors 660 and 662 function to change the output power level only in the macro mode of operation, the macro/micro signal at 334 is applied to both detectors as an input control signal. The macro/micro signal controls the detectors 660 and 662 to function only when the macro mode of operation has been selected. It has been determined that the reduction in power from the target level prior to delivery of the full active selected power is unneeded if the maximum active selected power is greater than some predetermined threshold amount, for example 50 watts. Accordingly, the VACT signal at 348, which represents the active maximum selected power, is applied to the level detector 666. The level detector 666 establishes the predetermined threshold amount of active power selected during which the reduction in target power is desired, and supplies an output signal at 664 to the missing pulse detector 662 when the VACT signal 348 represents a power level less than the predetermined threshold amount. The signal at 664 controls the missing pulse detector 662 to cause the delivery of the TPSW signal at 482 only when the VACT signal at 348 represents a maximum active amount of power selected less than the predetermined threshold power level where switching is desired.

A timing logic circuit 668 receives the frequency signal at 416 and supplies synchronization signals at 669 and 670 to the missing pulse detector 662 and the pulse burst detector 660, respectively. The detectors 660 and 662 thus also operate in synchronization with the frequency signal 416 and the signal at 658. The detectors 660 and 662 are basically retriggerable multivibrators. Upon detection of a predetermined number of missing pulses, the missing pulse detector 662 is triggered to supply an output signal at 672. The predetermined number of pulses is selectively established by and internal timing network of the detector 662. Similarly, upon the detection of the occurrence of a predetermined number of pulses applied at 658, the pulse burst detector 660 supplies a signal at 671. The signals at 671 and 672 are applied to an OR gate 673, and the output signal from the OR gate 673 is applied to the timing logic circuit 668. The logic function of the circuit 668 causes the switching of the level of the signal at 422 to create the target/active signal achieving the function as described.

To create the TPSW signal at 482, the missing pulse detector 662 supplies a signal at 674 to a timer 675, upon the occurrence of at least one missing pulse detected at 658. The level detector 666 establishes a signal at 664, and the signal at 664 causes the missing pulse detector 662 to first supply the signal at 674 rather than to apply the signal at 672. In response to a signal at 674, the timer 675 immediately supplies the TPSW signal at 482, and maintains that signal for a predetermined time period, for example 1.5 seconds, after the first missing pulse is detected. The function of the timer 675 is to make sure that the pencil has been intentionally and positively moved into a predetermined proximity with the tissue before the active power level is delivered. By providing a timing function at 675, sporadic quick movements of the pencil in sufficiently close proximity with the tissue do not result in fluttering of the power level between the active and target levels. Since the TPSW signal maintains the reduced level of target power for the predetermined time period established by the timer 675, the active level of power will be reliably applied only when the surgeon so intends.

The CGEN signal at 444 from the logic control 304 operatively controls the timing logic circuit 668 to function in the matter described only when the CGEN signal operatively causes the drive pulse generator 418 of the logic control 304 (FIG. 14) to operate in the manner described to deliver the drive pulses.

The differences in electrical operation of the ESG in the macro and micro modes of operation cooperate with the different types of gases employed in the two different types of operation. The type, flow rate and characteristics of the gases are significantly different in the macro and micro modes of operation.

Gas Characteristics

One of the most important characteristics of the gas jet 54 (FIG. 4) is that it have a sufficiently high flow rate to clear accumulated fluids, such as blood, from the tissue. Clearing the fluids is a practical necessity because it allows the electrical energy from the beam to enter the tissue stroma and create the eschar. Without adequate fluid clearing, the electrical energy has an effect only on the surface of the flowing fluid, thereby creating only a temporary coagulum which usually soon sloughs away under the influence of additional oozing fluids. With a sufficient gas flow rate the fluids are cleared or held back so the electrical energy can reach the surface of the tissue and penetrate into the tissue stroma to create an improved eschar in the tissue stroma, thereby obtaining improved coagulation.

The gas flow rate varies according to the mode of operation and the type of gas employed. Typically, fulguration or the macro mode of operation will be selected for use on highly perfused bleeding tissues. A relatively high gas flow rate is desired because of the continued and renewed presence of fluids. Since effective coagulation in this type of tissue generally requires an arc hole reticulum and an underlying thermally desiccated layer, the type of gas employed is one which will readily conduct electrical energy in arcs, since arcs achieve this type of tissue effect. Thermal desiccation or the micro mode of operation is generally selected when coagulation effects are desired on relatively delicate thin tissues, such as the mesentery. Because of the more delicate nature of this type of operation and the relative absence of fluids, a substantially reduced flow rate is usually utilized. The type of gas used in the micro mode of operation should be one which is easily ionized and which transfers electrical energy in the jet as a diffuse current without creating arcs.

The presently preferred type of gas for use in fulguration is pure argon. It has been determined that argon readily supports arcs at the power levels necessary to create the arc hole reticulum and thermal desiccation layers which characterize the fulguration eschar. These power levels are generally in the range from 40 to 200 watts. Furthermore, argon has a density greater than that of air and therefore more readily clears the surgical site of fluids and the oxygen from the air. Eliminating oxygen from the surgical site avoids excessive heating and carbonization of the tissue. Flow rates of between four to thirteen standard liters per minute issuing from a pencil nozzle 52 (FIG. 6) of approximately 0.100 inch diameter have achieved effective fluid clearing and arc energy transfer characteristics at a distance of approximately 0.5 to 1.5 centimeters separation of the tip of the pencil from the tissue at the surgical site. This relatively high gas flow rate issuing from the nozzle of the size described creates arc pathways having an average lifespan which is lower than the average lifespan of a conventional electrosurgical active electrode, thereby causing the quantum of electrical energy transferred by each individual arc in a pathway to be reduced. However, considerably more individual arc pathways result. More uniform distribution of the electrical energy over the tissue at the surgical site occurs because of the greater number of arc pathways. The relatively high gas flow rate also can cause frothing of the blood which, under some circumstances, is desirable in assisting the hemostatic process. The breakdown voltage point at which argon becomes ionized, and therefore results in the arc pathways, is relatively high. This breakdown point effectively coordinates with the relatively higher power levels to support the arc pathways at the gas flow rates during fulguration. Any argon absorbed in the 75nature circulating blood of the patient is cleared with the first pass through the lungs.

For thermal desiccation, a gas is selected which has a lower breakdown voltage and lower impedance. Helium is preferred. Because of the relatively low breakdown voltage it is possible to ionize helium to transfer relatively low levels of energy, e.g. three to twenty watts, to the tissue as a diffused current and without initiating arcs in the gas jet. Flow rates from approximately 0.08 to 1.6 standard liters per minute issuing from a pencil of the previously described size, and spaced at the 0.5 to 1.5 centimeter distance from the tissue, and at the three to twenty watts power delivery level, results in thermal desiccative effects believed never before to have been obtained from electrosurgery. In most of the applications where the thermal desiccative effects in the micro mode of operation are desirable, substantial fluid clearing problems will not be encountered. The relatively lower gas flow rate therefore poses no particular problem in clearing fluids. The gas flow rate is, however, sufficiently high to maintain the inert atmosphere at the surgical site by overcoming the effects of the surrounding heavier-density air, which tends to dissipate the lighter helium.

By increasing the electrical power delivery of the ESG substantially above approximately 20 watts, helium will also break down into arc pathways and sustain individual arcs containing individual quantities of destructive energy rather than a diffuse non-arcing current. Thus, fulguration effects can also be achieved by helium when the ESG is controlled to deliver substantially greater electrical power to the tissue.

An inert gas is preferred in both modes of operation. The inert gas prevents oxidation of the tissue, and therefore the charring and carbonization which normally results from electrosurgery conducted in air. An inert gas has a relatively predictable voltage breakdown characteristic, making initiation of ionization from the booster and target pulses controllable. The energy levels of the booster and target pulses can be matched to the breakdown characteristics of the particular gas selected. Furthermore, the predictable breakdown characteristics of the gas allow better regulation over the conductive and arc transferring pathways in the gas jet.

ESG Impedance Characteristics

To obtain improved coagulation and tissue effects, the internal impedance characteristics of the ESG must be relatively broad, offering the capability of significant power transfer into tissues of a wide range of impedances. Without the ability to transfer significant power into both high and low impedances, the improved tissue effects are very difficult to achieve.

The internal generator impedance load curve required for a clinical effectiveness is very broad and preferably relatively flat, as is illustrated in FIG. 20. Curve 700 illustrates the power output delivered over a range of impedances delivered by an ESG of the present invention operating in the macro mode at approximately 100 watts of selected power. Curve 702 illustrates a similar circumstance where power of approximately 50 watts has been selected for delivery. The curves 700 and 702 are to be compared to curves 704 and 706, and 708 and 710, respectively. Curves 704 and 706 illustrate the same selected power delivered by what is considered to be the best prior art conventional ESG (that disclosed in U.S. Pat. No. 4,429,694). Curves 708 and 710 illustrate the same two power levels delivered from an earlier conventional ESG prior to the invention described in U.S. Pat. No. 4,429,694.

Prior to the invention in U.S. Pat. No. 4,429,694, conventional practice was to match the output impedance of the ESG to what was perceived as the typical tissue impedance in order to obtain maximum power transfer. The typical perception of tissue impedance ranged from three hundred to six hundred ohms. At tissue impedances greater than six hundred ohms, power delivery rapidly dropped off as it illutrated by curves 708 and 710. At tissue impedances in the range of approximately 1,000 ohms, the earlier conventional ESG usually was incapable of delivering sufficient power to achieve an effective eschar. One of the significant recognitions made in conjunction with the invention described in U.S. Pat. No. 4,429,694 was that a superior hemostatic effect could be created, in significant part, by creating a higher output impedance in the ESG. The impedance of the ESG was not matched to the tissue impedance, but was raised in order to form arcs of greater length and shorter duration. As can be seen by curves 704 and 706, significant energy delivery occurred into tissues in the impedance range of between 1,000-1,500 ohms. At impedances greater than about 1,500 ohms, the power delivery characteristics rapidly dropped off. The reduction in power delivery characteristics into impedances of greater than 1,500 ohms with the invention described in U.S. Pat. No. 4,429,694, was the result of the recognition that there was a practical limit to which the generator impedance could be raised. That limit was determined by the necessity to maintain good control over the application of the arc energy. At higher impedance levels, the arc became unruly in the room-air atmosphere and the surgeon could not effectively control the direction or surgical effect of the RF arcing energy. Thus, even with the superior prior invention of U.S. Pat. No. 4,429,694, there was a practical limit to which the internal generator impedance could be raised.

By confining the path of the electrical energy within the gas jet in accordance with the present invention, the internal ESG impedance can be raised significantly without encountering the problems typical of the prior art. As curves 700 and 702 illustrate, significant energy can be delivered into impedances at least two or three times greater in value than the impedances into which the invention of U.S. Pat. No. 4,429,694 could effectively deliver power (curves 704 and 706), and into impedances approximately five to ten times higher than the next earlier generation of prior art ESG's (curves 708 and 710).

The relatively broad impedance range of the ESG of the present invention is necessary to deliver adequate energy to the tissue to achieve the superior coagulation and eschar effects, as well as achieve practical operation. The ESG must have the capability to deliver significant power into relatively low impedance tissues, such as those tissues perfused with blood or fluid. These tissues may have an initial impedance of as low as about ten ohms. The capability to deliver the energy into low impedances is necessary to quickly form a coagulum in the tissue, so the coagulum will not be carried away with the flow of blood. The capability to deliver power into significantly high impedances is necessary to initiate ionization in the gas jet, to sustain the ionization at relatively high gas flow rates, and to maintain ionization when the pencil is not in working distance from the tissue. If the internal generator impedance curve cuts off the energy transfer capability too quickly at high impedances, it is very difficult to initiate a beam or sustain a long beam. Initiation difficulties require the pencil electrode to be brought into contact or very close proximity with the tissue. Contacting the electrode with the tissue can cause fouling of the electrode due to denatured proteins sticking to the heated electrode. Short beam lengths require close working distances of the pencil from the tissue, which tend obscure the surgeon's view. The high flow rates of the gas tend to sweep the ionized particles rapidly away from the electrode. Without a relatively high impedance transfer capability, it would be impossible to transfer sufficient energy to the rapidly flowing gas jet to maintain the arc and ionized energy transfer pathways in the gas jet at the high gas flow rates.

Various factors influence the shape of the optimal ESG load curve. These factors include the gas utilized and its flow rate, the desired beam length, and the desired initiation distance. The entire system of the electrical environment, including the ESG components, the conductors in the cord, the conductors in the pencil, the gap between the electrode and the tissue, the tissue impedance and characteristics, the stray reactances, and others, play a part in the overall power transfer characteristics. Since it is the arc and the energy coupling pathways that transfer energy to the tissue, the length, pathway and lifetime of the ionization in the gas jet self-adjusts in response to the instantaneous state of the system as a whole. The capacity of the arcs and energy coupling pathways to respond is greatly dependent on the output response characteristics of the ESG. A broader ESG internal impedance characteristic, as represented by curves 700 and 702 in FIG. 20, allows the ESU of the present invention to dynamically adapt to different load conditions and maintain the power transfer levels to achieve the improved superior tissue effects and eschar which result in superior coagulation.

The broader internal impedance curve of the ESG of the present invention was obtained by recognized techniques. Compared to the ESG described in U.S. Pat. No. 4,429,694, larger magnetics were employed in the output transformer 634 (FIG. 18) to handle the higher voltages and powers, the number of secondary turns were increased compared to the primary turns, and the current and voltage limits of the ESG were increased by establishing higher limits in the limit circuits 550 and 552 (FIG. 16). There are many different techniques for increasing the internal generator impedance range, as recognized in the generator and amplifier art. The arc sense circuit 316 (FIGS. 12 and 19) also plays a role in achieving proper energy delivery characteristics, but adjusting the delivered power in the manner described.

Improved Tissue Effects and Eschar

The characteristics of the eschar obtained from operating the present invention in the fulguration or macro mode are illusrated in FIGS. 21, 22, 23A and 23B. FIGS. 21, 22, 23A and 23B are intended to be compared to the best-known prior art eschar illustrated in FIGS. 1, 2, 3A and 3B, respectively. In the eschar available from the present invention, it can be seen that the arc hole reticulum layer 712 (FIGS. 23A and 23B) includes a larger number of smaller-diameter holes distributed over a specific surface area. The arc holes are more uniformly spacially distributed over the surface of the tissue. The arc holes are more uniform in size or cross-sectional area compared to one another. The tissue is essentially free of charring and carbonization. The walls of tissue between adjoining arc holes are greater in thickness and therefore more pliable. As is seen in FIGS. 23A and 23B, the arc hole reticulum 712 is more uniform in depth but shallower than the prior art arc hole reticulum. The thermal desiccation layer 714 below the arc hole reticulum layer 712 is relatively thin and is also more uniform in depth. The more uniform depth and relative thinness of the layer 714 also promotes better pliability in the eschar to avoid cracking. Unaffected tissue is illustrated at 716.

The relatively large number of smaller sized arc holes distributed evenly over the surface and to a more uniform depth, with the absence of charring or carbonization, and the resulting relatively stronger and more pliable walls between individual arc holes, creates an effective reticulum in which coagulation of blood is more quickly and effectively achieved. The surface area of the smaller holes and the more structurally sound but yet flexible supporting network of tissue remaining around the arc holes in the reticulum layer contributes significantly to obtaining enhanced coagulation capability. The relatively thin thermal desiccation layer 714 below the arc hole reticulum 712 minimizes the amount of tissue subjected to thermal necrosis and promotes better and faster healing. Less tissue is actually destroyed in both the arc hole and desiccation layers, which also promotes more rapid healing. The limited depth of destruction from the eschar allows the present invention to be used around organs such as the bowel or bladder with substantially reduced risks of perforation.

The small arc holes and more even distribution of the arc energy are probably related to arc pathway lifetimes. Initially, each arc in the gas jet takes a pathway to fresh tissue transferring energy in a desiccation process. As the small spot becomes desiccated, each subsequent arc finds a low impedance pathway to the tissue surface. This occurs either by taking a longer pathway to fresh (low impedance) tissue (spreading) or by taking a shorter pathway to already desiccated (high impedance) tissue. The latter is thought to be responsible for th development of the arc hole reticulum layer. The impedance of the arc pathway increases with distance, heating and the degree of tissue desiccation. The dynamic balancing of these factors, combined with the internal ESG impedance characteristics, achieve the superior tissue effects.

A study has been done to compare the healing or degree of damage following the resection of a canine liver and spleen by use of the present invention operated in a fulguration mode of operation and comparing it to the best prior art conventional electrosurgical unit (represented by U.S. Pat. No. 4,429,694). These two types of fulguration techniques will be hereinafter referred to as the present technique and the best prior technique.

Sixteen canine animals were used in the study. The liver and spleen of each were partially resected in two areas. At one site, hemostasis was obtained using the present invention. At the other site, hemostasis was obtained using the best prior art system. The electrical power or wattage delivered in both systems was about 60 to 70 watts. Eight animals were autopsied seven days after the surgery, and the other eight animals were autopsied at 28 days after the surgery. Sections were taken from the liver and spleen according to a predetermined sampling protocol. The specimens were analyzed by veterinarian pathologists who have had extensive experience in histopathological analysis of electrocoagulation lesions.

The pathologists' report showed a measurable difference between the healing produced by the present invention and the best prior art technique, at 28 days following the operation. In the spleen, the eschar produced by the present invention at the resection site was only 70% as thick as the eschar produced by the prior art technique. In the liver, the eschar produced by the present invention at the resection site was approximately 93% as thick as the eschar produced by the prior art technique. At the seven day time interval, significant differences were not observed.

A second portion of the study analyzed hematologic and liver enzyme changes after the operation. In eight animals, a battery of studies was obtained before and after the operation, which included WBC, RBC, hemoglobin, hematocrit, total bilirubin, alkaline phosphatase, LDH, and SGOT. These studies were compared with previously performed studies on electro coagulation by use of the prior art technique. The present invention created less trauma than the prior electrosurgical technique. There was very little change in LDH and SGOT during the postoperative period. The alkaline phosphatase showed transient elevation. The changes in liver enzymes produced were actually less than in previously done studies based on the prior electrosurgical technique.

The conclusions which can be drawn from this study are that the present invention produced less anatomic change at 28 days than the prior electrosurgical technique, and the present invention produces somewhat lesser liver enzyme changes than the prior art technique. Both of these conclusions support an observation that the present invention contributes to and enhances the long term healing resulting from fulguration electrosurgery.

FIGS. 24 and 25 illustrate the tissue effects obtained by operating the present invention in the desiccation or micro mode. It is believed that the tissue effects illustrated in FIGS. 24 and 25 have never before been obtained by an ESU. The eschar is characterized by a single desiccated layer 718 illustrated in FIG. 25. This desiccated layer is generally very thin and of uniform depth. The relative uniform depth and continuity of the layer are characteristics never before obtained in electrosurgery, even when the active electrode of a conventional ESG was contacted against the tissue. As is shown in FIG. 24, the tissue has not been perforated or destroyed by arc holes or any type of hole matrix. Instead, a thin, pliable, integral layer or crust has been created by desiccating the layer of tissue and sealing the unaffected tissue 720 below the eschar 718.

As a result of its nondestructive characteristics, the desiccation or micro mode of operation finds application on delicate tissue where arcing would actually tear open vessels or tissues instead of coagulating. The rate of desiccation or energy transfer to the tissue is dependent upon the time of application, thereby allowing the surgeon to obtain specific yet delicate effects. Another characteristic of the micro mode of operation is the lack of low frequency spectral components normally associated with rectification during arc formation. This advantageously minimizes muscle stimulation which normally occurs in the arcing modes. In particular, the micro mode of operation can be applied to the diaphram with minimal stimulation. It is expected that the micro mode of operation can be used in accomplishing particular surgical procedures where electrosurgery has not previously been successfully applied.

The discoveries, advantages, improvements and the preferred embodiment of the present invention have been shown and described to the extent consistent with current beliefs and observations. Although many of the features and observations cannot be explained with total certainty, a useable embodiment has been shown and described by way of preferred example. The invention itself is defined by the scope of the appended claims.

The invention claimed is:

1. An electrosurgical unit for creating an improved eschar in the stroma of tissue, comprising:

means for conducting a predetermined gas not containing oxygen in a jet to the tissue at a predetermined flow rate sufficient to clear natural fluids from fluid-perfused tissue and to substantially expose the tissue stroma; and means for transferring electrical energy at a predetermined radio frequency range in ionized conductive pathways at a predetermined power level within the gas jet in an electrical circuit which includes the tissue to create the eschar.

2. An electrosurgical unit as defined in claim 1 wherein the predetermined power level at which radio frequency energy is transferred and the predetermined flow rate at which the gas is conducted and the predetermined gas are selected to create the eschar in fresh blood-perfused tissue and to initiate the ionized conductive pathways in the gas jet when the gas jet is spaced a sufficient distance from the tissue to have no substantial fluid clearing effect on the tissue.

3. An electrosurgical unit as defined in claim 2 wherein the radio frequency energy transferred is confined only to arcs conducted in the ionized conductive pathways in the gas jet.

4. An electrosurgical unit as defined in claim 1 wherein:

said means for conducting a predetermined gas in the jet comprises a pencil-like device having nozzle means for creating a generally laminar jet;

said electrical energy transferring means comprises an electrode means positioned within the gas flow path within the nozzle means; and further comprising:

means connecting the electrode means to the nozzle means whereby said nozzle means and said electrode means form a unit; and wherein:

the nozzle means and the electrode means are removable as a unit from the pencil-like device.

5. An electrosurgical unit as defined in claim 4 wherein:

the nozzle means and the electrode means forming the unit are a part of a nozzle and electrode support assembly, and the pencil-like device includes a handle connected to both said gas conducting means and said energy transferring means, and coupler means for selectively connecting the nozzle and electrode support assembly in a predetermined connected relationship in the handle to supply gas from the handle to the nozzle means and to supply electrical energy from the handle to the electrode means.

6. An electrosurgical unit as defined in claim 5 further comprising:

means for operatively sensing the predetermined connected relationship of the nozzle and electrode support assembly in the handle, and means for preventing the delivery of the electrical energy to the electrode means until the predetermined connected relationship is established.

7. An electrosurgical unit as defined in claim 1 wherein:

said gas conducting means comprises cord means for conducting the predetermined gas therethrough, and said electrical energy transferring means comprises an electrical conductor positioned in the cord means and substantially surrounded by the predetermined gas conducted in said cord means.

8. An electrosurgical unit as defined in claim 7 wherein:

said cord means comprises a plurality of lumens extending generally longitudinally along the length of the cord means and positioned generally concentrically about a longitudinal reference axis of the cord means, and the electrical conductor is positioned generally at the longitudinal reference axis.

9. An electrosurgical unit as defined in claim 1 wherein:

said gas conducting means comprises a pencil-like device adapted to be manipulated by the surgeon during a surgical procedure and having nozzle means for creating the gas jet;

said electrical energy transferring means comprises electrode means positioned within the gas flow path in said nozzle means and operative for transferring the electrical energy to the gas jet;

said electrical energy transferring means comprises generator means for generating a first predetermined level of electrical power in a predetermined radio frequency range to create the eschar and for generating a second predetermined level of electrical power at the predetermined radio frequency range which is substantially less than the first power level, and means for supplying the electrical power generated to the electrode means; and said electrical energy transferring means further comprises means for sensing an electrical condition in the ionized pathways between the electrode means and the tissue to establish an operative separation distance of the pencil-like device from the tissue and for controlling the generator means to switch from generating the second predetrermined level of power to commence generating the first predetermined level of electrical power to create the eschar.

10. A method of electrosurgically creating an improved eschar in the stroma of tissue, comprising:

conducting a predetermined gas in a jet to the tissue at a predetermined flow rate sufficient to clear natural fluids from fluid-perfused tissue and to substantially expose the tissue stroma;

transferring electrical energy at a predetermined radio frequency range as arcs in ionized conductive pathways at a predetermined power level within the gas jet in an electrical circuit which includes the tissue; and creating the improved eschar by the effects of the predetermined gas flowing at the predetermined rate and the predetermined power level of energy, the improved eschar generally characterized by:

an outer generally uniform depth reticulum of arc-created holes penetrating the tissue from a surface of the eschar, the arc holes having substantially comparable cross-sectional sizes and substantially uniform spatial distribution over the surface of the eschar, the tissue of the reticulum between adjacent arc holes providing pliability of the eschar without cracking; and a generally uniform-depth thermally desiccated layer separating the arc hole reticulum from the unaffected tissue.

11. A method as defined in claim 10 wherein the arc hole reticulum of the improved eschar is further generally characterized in relation to an arc hole reticulum of an eschar created by prior art fulguration to achieve approximately the same hemostatic effect, by shallower depth, by arc holes of generally smaller cross-sectional size, by a larger number of arc holes distributed over a specific surface area of the eschar, by more uniformity in arc hole size, and by greater tissue wall thicknesses betwen adjacent arc holes.

12. A method as defined on claim 11, wherein the thermally desiccated layer of the improved eschar is further generally characterized in relation to a thermal desiccation layer of an eschar created by prior art fulguration to achieve approximately the same hemostatic effect, by shallower depth.

13. A method as defined in claim 10 wherein the improved eschar is further generally characterized by a substantial absence of charring and carbonization of the arc hole reticulum.

14. A method as defined in claim 10 wherein the arcs in the ionized patheways are generally shorter in length and in time duration on the average compared to the arcs in the ionized pathways of a prior art electrosurgical unit operating in a fulguration mode and using a conventional active electrode in an atmospheric environment.

15. An electrosurgical unit for creating an improved eschar in the stroma of tissue, comprising:
  means for conducting a predetermined gas in a jet to the tissue at a predetermined flow rate sufficient to clear natural fluids from fluid-perfused tissue and to substantially expose the tissue stroma; and
  means for transferring electrical energy at a predetermined radio frequency range as a non-arcing diffuse current in ionized conductive pathways at a predetermined power level within the gas jet in an electrical circuit which includes the tissue to create the eschar.

16. A method for electrosurgically creating an improved eschar in the stroma of tissue, comprising:
  conducting a predetermined gas in a jet to the tissue at a predetermined flow rate sufficient to clear natural fluids from fluid-perfused tissue and to substantially expose the tissue stroma;
  transferring electrical energy at a predetermined radio frequency range substantially as a non-arcing current in ionized conductive pathways at a predetermined power level within the gas jet in an electrical circuit which includes the tissue;
  creating the improved eschar by the effects of the predetermined gas flowing at the predetermined rate and the predetermined power level of energy, the improved eschar generally characterized by a thermally desiccated layer formed in the tissue stroma at a surface of the tissue and which is generally effective to seal the underlying unaffected tissue.

17. A method as defined in claim 16 wherein the thermally desiccated layer is generally uniform in depth.

18. A method as defined in claim 16 wherein the thermally desiccated layer is further characterized by an absence of performations created by the electrical energy.

19. An electrosurgical unit for creating an improved eschar in the stroma of tissue, comprising:
  means for conducting a predetermined gas in a jet to the tissue at a predetermined flow rate sufficient to clear natural fluids from fluid-perfused tissue and to substantially expose the tissue stroma;
  means for transferring electrical energy at a predetermined radio frequency range in ionized conductive pathways at a predetermined power level within the gas jet in an electrical circuit which includes the tissue to create the eschar; and
  means for selectively switching between a first mode of operation and a second mode of operations;
  the first mode of operation resulting in the transfer of radio frequency electrical energy in arcs in the ionized conductive pathways; and
  the second mode of operation resulting in the transfer of radio frequency electrical energy as a non-arcing diffuse current in the ionized conductive pathways.

20. An electrosurgical unit as defined in claim 19 wherein said means for selectively switching between the first and second modes of operation comprises:
  means for selectively conducting a different predetermined gas in each mode of operation, and
  means for changing the predetermined level of power delivered in each mode of operation to achieve the defined electrical energy transfer characteristics in the gas jet in each mode of operation.

21. An electrosurgical unit as defined in claim 20 wherein the predetermined gas conducted in the first mode of operation is argon, and the predetermined gas conducted in the second mode of operation is helium.

22. An electrosurgical unit as defined in claim 20 wherein each predetermined gas is inert.

23. An electrosurgical unit for creating an improved eschar in the stroma of tissue, comprising:
  means for conducting a predetermined gas in a jet to the tissue at a predetermined flow rate sufficient to clear natural fluids from fluid-perfused tissue and to substantially expose the tissue stroma;
  means for transferring electrical energy at a predetermined radio frequency range in ionized conductive pathways at a predetermined power level within the gas jet in an electrical circuit which includes the tissue to create the eschar; and
  said electrical energy transferring means, when selectively activiated:
  transfers electrical energy to the gas jet at a first predetermined active power level to create arcs in the ionized conductive pathways to thereby form the eschar on the tissue stroma,
  transfers electrical energy to the gas jet at a second predetermined target power level less than the active power level to create substantially a non-arcing ionization state in the gas jet when not transferring the active power level, and
  automatically switches between the target power level and the active power level upon sensing a predetermined electrical condition in the ionized conductive pathways to the tissue.

24. An electrosurgical unit as defined in claim 23 wherein the predetermined electrical condition in the ionized conductive pathways is the conduction of at least one arc of electrical energy while transferring the target power level.

25. An electrosurgical unit as defined in claim 24 wherein said electrical energy transferring means further:
  transfers electrical energy to the gas jet at a third predetermined level which is less than the target power level after first sensing the presence of a predetermined number of arcs in the ionized conductive pathways while transferring the target power, and
  automatically switches to the active power level upon sensing a predetermined number of arcs in the ionized conductive pathways while transferring the third power level to the gas jet.

26. An electrosurgical unit as defined in claim 25 wherein said electrical energy transferring means further:
automatically switches to the target power level upon failing to sense the predetermined number of arcs within a predetermined time period while transferring the third power level.

27. An electrosurgical unit as defined in claim 25 wherein said electrical energy transferring means further:
transfers electrical energy to the gas jet at a fourth predetermined booster power level which is greater than the target power level and less than the active power level, upon initiating the delivery of electrical power to the gas jet.

28. An electrosurgical unit for creating an electrosurgical effect on tissue, comprising:
means for conducting a predetermined gas at a predetermined flow rate in a jet to the tissue,
electrode means positioned within the gas jet and operative for transferring electrical energy to the tissue in ionized conductive pathways in the gas jet to achieve an electrosurgical effect,
generator means for generating first predetermined power level of electrical energy in a predetermined radio frequency range to create the electrosurgical effect and for generating a second predetermined power level of electrical energy at the predetermined radio frequency range, the second power level being substantially less than the first power level and substantially insufficient to create the electrosurgical effect,
means for supplying the electrical power generated to the electrode means, and
sensing means including means for operatively sensing a predetermined characteristic related to the distance between the electrode means and the tissue and for controlling the generator means to deliver the first power level when the electrode means is separated from the tissue by less than a predetermined distance and for controlling the generator means to deliver the second power level when the electrode means is separated from the tissue by greater than the predetermined distance.

29. An electrosurgical unit as defined in claim 28 wherein said sensing means operatively senses a predetermined electrical characteristic of the spacial gap between the electrode means and the tissue to establish the predetermined distance.

30. An electrosurgical unit as defined in claim 29 wherein the predetermined electrical characteristic is a current conduction characteristic.

31. An electrosurgical unit as defined in claim 29 wherein the predetermined electrical characteristic is at least one arc in the gas jet from the electrode means to the tissue.

32. An electrosurgical unit for creating an eschar on tissue, comprising:
means for creating a jet of a predetermined ionizable gas flowing at a predetermined flow rate;
electrode means positioned within the gas jet for transferring electrical energy to the gas jet in an electrical circuit which includes the tissue; and
electrosurgical generator means connected to the electrode means and operative for generating electrical energy at a predetermined radio frequency range and at a plurality of different predetermined power levels and operative to deliver the electrical energy generated to the electrode means to create ionized conductive pathways within the gas jet by which electrical energy is conducted to the tissue within the gas jet, said electrosurgical generator means comprising:
resonant circuit means having a natural resonant frequency within the predetermined radio frequency range and operative when energized by drive pulses to supply the electrical energy at the predetermined frequency range to said electrode means,
drive pulse generator means for supplying drive pulses of predetermined energy content to said resonant circuit means;
control means connected to the drive pulse generator means for controlling the drive pulse generator means to supply a plurality of predetermined different types of drive pulses, each predetermined different type of drive pulse having a different energy content;
sensing means connected to the resonant circuit means and to the control means and operative for sensing a predetermined electrical signal characteristic in the resonant circuit means which relates to a predetermined electrical condition in the ionized conductive pathways between the electrode means and the tissue, said sensing means supplying an active level signal to said control means upon sensing the predetermined electrical signal characteristic and supplying a target level signal to said control means when the predetermined electrical characteristic is not sensed,
said control means responding to the target level signal to control said drive pulse generator means to supply a target drive pulse of predetermined energy content sufficient to ionize the gas jet in a non-arcing state, and
said control means responding to the active level signal to control said drive pulse generator means to supply an active drive pulse of predetermined energy content sufficient to ionize the gas jet in arcs.

33. An electrosurgical unit as defined in claim 32 wherein:
said sensing means is further operative for supplying a target power switch signal initially upon sensing the predetermined electrical signal characteristic, and
said control means responding to the target power switch signal to control said drive pulse generator means to reduce the energy content of the target drive pulses to a predetermined amount.

34. An electrosurgical unit as defined in claim 33 wherein said sensing means maintains the target power switch signal for a predetermined time period after initially sensing the predetermined electrical signal characteristic.

35. An electrosurgical unit as defined in claim 35 wherein the sensing means supplies the active level signal upon sensing the predetermined electrical signal characteristic for a predetermined time during which the target power switch signal is delivered.

36. An electrosurgical unit as defined as claim 32 further comprising:
control switch means for supplying a request signal when selectively activated by the surgeon to request the delivery of electrical energy to the gas jet, and wherein:

said control means operatively responds to the request signal to control said drive pulse generator means to supply a booster drive pulse of predetermined energy content to initially ionize the gas jet for a predetermined booster time period after the occurrence of the request signal and thereafter to supply the target drive pulse after expiration of the predetermined booster time period, each booster drive pulse having an energy content greater than the energy content of a target drive pulse and less than the energy content of an active drive pulse.

37. An electrosurgical unit for conducting electrical energy at a predetermined radio frequency range in an ionizable gas jet to tissue in an electrical circuit which includes the tissue to create an eschar in the tissue, comprising:

electrode means by which to transfer electrical energy to the gas jet; and an electrosurgical generator means connected to the electrode means, said generator means having a sufficiently high end internal impedance to transfer sufficient electrical energy in ionized conductive pathways in the gas jet while the gas jet is flowing at a predetermined sufficiently high flow rate to clear fluids from the surface of the stroma of a tissue perfused with natural fluids, and to sustain ionization when the gas jet is spaced sufficiently distant from the tissue to avoid any electrosurgical effect on the tissue; and wherein the high end internal impedance of the electrosurgical generator means extends in excess of a value within the range of three to six thousand ohms; and the predetermined gas flow rate is greater than four standard liters per minute.

38. An electrosurgical unit for conducting electrical energy at a predetermined radio frequency range in a gas jet to tissue in an electrical circuit which includes the tissue, comprising:

a pencil-like device adapted to be manipulated by the surgeon during the surgical procedure and comprising nozzle means for creating the gas jet and means for transferring the electrical energy in the gas jet to the tissue, electrosurgical generator means for generating electrical energy at the predetermined radio frequency range;

gas supplying means for supplying gas by which to create the gas jet;

cord means operatively connecting the pencil-like device with the electrosurgical generator means and the gas supplying means, said cord means including an electrical conductor extending therealong and electrically connecting the electrosurgical generator means with the electrical energy transferring means to conduct electrical energy therebetween, said cord means also including a plurality of gas conducting lumens extending generally parallel to the electrical conductor and generally surrounding the electrical conductor;

means responsive to one of a predetermined gas pressure or gas flow condition within the pencil-like device and operative for preventing the electrosurgical generator means from delivering electrical energy upon detecting a failure to establish the predetermined one of the gas flow or gas pressure conditions;

said pencil-like device further comprises:

a handle connected to said cord means;

a nozzle and electrode support assembly having the nozzle means for creating the gas jet from gas supplied through the gas conducting lumens of said cord means and also comprising electrode means, the means for transferring the electrical energy from the electrical conductor of said cord means to the gas jet including the electrode means; and coupler means connected to the handle and operative for removably connecting the nozzle and electrode support assembly to the pencil-like device;

said coupler means further comprises conduit means for operatively extending each lumen of said cord means through said coupler means; and said nozzle and electrode support assembly comprises means operative when said nozzle and electrode assembly is properly connected in the pencil-like device for channeling gas supplied in one supply lumen in said cord means back to another sensing lumen in said cord means by which to sense the predetermined one of the gas flow or gas pressure conditions in said pencil-like device.

39. An electrosurgical unit as defined in claim 38 further comprising means operatively connected to the sensing lumen of said cord means and operative in response to the gas condition in said sensing lumen to control the electrosurgical generator means.

40. A method of electrosurgical coagulation by conducting electrical energy in arcs to a tissue perfused with blood in a living being, comprising:

flowing a jet of ionizable gas to the tissue at a predetermined flow rate sufficient to clear the blood from the surface of the tissue;

conducting the electrical energy in arcs substantially only in ionized pathways in the gas jet to the tissue in an electrical circuit which includes the tissue by applying electrical energy of a predetermined characteristic to the gas to establish the arcs and the ionized pathways, and creating an eschar of predetermined characteristics in the tissue stroma to achieve coagulation as a result substantially only of applying the arcs and the gas jet to the tissue, the predetermined characteristics of the eschar characterized by:

a first layer created by a reticulum of holes created by arcs penetrating into the stroma from the surface of the tissue, the first layer extending into the stroma approximately a uniform depth from the surface of the tissue, the arc-created holes having a substantially uniform spacial distribution over the surface of the eschar and the holes extending approximately uniformly to the depth of the first layer, and the arc-created holes being substantially comparable to one another in cross-sectional size at the eschar surface;

a second layer of approximately uniform depth extending further into the tissue from the lowermost boundry of the first layer, the second layer created by thermal necrosis and desiccation of the tissue from the heat energy of the arc current, the second layer being substantially absent of arc-created holes, the lowermost boundry of the second layer separating the eschar from the unaffected tissue;

a substantial absence of charred material on the first layer;

an adherence to the stroma of the underlying tissue to a degree which requires substantial destruction of the stroma to separate the eschar from the tissue; and pliability without cracking.

41. A method as defined in claim 40 further comprising:

substantially clearing the surface of the tissue of fluids during the formation of the eschar by controlling the predetermined flow rate of the gas jet.

42. A method as defined in claim 40 further comprising:

inhibiting the occurrence of charred material by flowing a gas in the jet which is substantially absent of oxygen.

43. A method as defined in claim 40 further comprising:

limiting the predetermined maximum flow rate of the gas jet to a level which will support the conduction of the arcs to the-tissue without extinguishing the ionized pathways.

44. A method as defined in claim 40 wherein applying electrical energy of a predetermined characteristic to the gas jet further comprises:

applying energy at a predetermined radio frequecy range to the gas jet, the predetermined radio frequency being a frequency which results in conduction of the electrical energy substantially only through the ionized pathways of the gas jet.

45. A method as defined in claim 40 wherein the gas jet applied to the tissue is in a generally laminar flow condition.

46. A method as defined in claim 40 wherein each ionized pathway which conducts an arc is approximately equal in length from the point of creation of the arc to the surface of the tissue.

47. A method as defined in claim 40 wherein the depth of the eschar to the lowermost boundary of the second layer is characteristically less than the depth of an eschar formed by prior art conventional electrosurgical fulguration, to achieve approximately the same hemostatic effect.

48. A method as defined in claim 40 wherein applying the electrical energy to the gas stream further comprises:

delivering electrical energy of the predetermined characteristics to the gas jet operatively from an electrical generator, the electrical generator having a sufficiently high internal impedance to result in initiating ionization in the gas jet when the gas jet is spaced so substantially away from the tissue as to achieve no electrosurgical effect.

49. A method as defined in claim 40 wherein the length of the ionized pathways is sufficiently great to avoid obscuring visualization of the formation of the eschar.

50. A method of electrosurgically desiccating a tissue without physically contacting an active electrode to the tissue, comprising:

flowing a jet of ionizable gas to the tissue at a predetermined flow rate, conducting electrical energy as a diffuse non-arcing current in ionized conductive pathways in the gas jet to the tissue in an electrical circuit which includes the tissue by applying electrical energy of a predetermined characteristic to the gas to establish the non-arcing diffuse current and the ionized conductive pathways, and creating an eschar of predetermined characteristics in the tissue stroma to achieve tissue desiccation and necrosis substantially only as a result of applying the diffuse current in the gas jet to the tissue, the predetermined characteristics of the eschar characterized by:

a single layer of thermally desiccated tissue subjected to necrosis by conduction of the diffuse current therethrough;

a substantial absence of charred material on the surface of the eschar;

an adherence to the stroma of the underlying tissue to a degree which requires substantial destruction of the stroma to separate the eschar from the tissue; and pliability without cracking.

51. A method as defined in claim 50 wherein the thermally desiccated layer of the eschar is substantially uniform in depth.

52. A method as defined in claim 50 wherein the thermally desiccated layer is further characterized by an absence of perforations created by the electrical energy.

53. A method as defined in claim 50 wherein the electrical energy is conducted at a predetermined radio frequency which results in conduction of the diffuse current substantially only through the ionized conductive pathways of the gas jet.

54. A method as defined in claim 50 further comprising:

substantially clearing the surface of the tissue of fluids during the formation of the eschar by controlling the predetermined flow rate of the gas jet.

55. A method as defined in claim 50 wherein the gas jet applied to the tissue is in a substantially laminar flow condition.

56. A method as defined in claim 50 further comprising limiting the electrical energy applied to the gas jet to a predetermined level which results in the conduction of the diffuse current in the ionized pathways without initiating arcs in the ionized pathways.

57. A method as defined in claim 50 wherein each ionized pathway that conducts the diffuse current is approximately equal in length.

58. A method as defined in claim 50 wherein the length of the ionized pathways is sufficiently great to avoid obscuring visualization of the formation of the eschar.

59. A method as defined as claim 50 wherein applying the electrical energy to the gas stream further comprises:

delivering electrical energy of the predetermined characteristics to the gas jet from an electrical generator, and creating a sufficiently high internal impedance in the generator to result in initiating ionization in the gas jet when the gas jet is spaced so substantially away from the tissue to achieve any electrosurgical effect.

* * * * *